United States Patent
Laiho et al.

(10) Patent No.: US 12,303,508 B2
(45) Date of Patent: May 20, 2025

(54) COMBINATORY TREATMENT STRATEGIES OF CANCER BASED ON RNA POLYMERASE I INHIBITION

(71) Applicant: THE JOHNS HOPKINS UNIVERSITY, Baltimore, MD (US)

(72) Inventors: Marikki K. Laiho, Baltimore, MD (US); Hester Hui Liu, Cockeysville, MD (US); Paul Sirajuddin, Baltimore, MD (US); Elina Ikonen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/335,737

(22) PCT Filed: Sep. 22, 2017

(86) PCT No.: PCT/US2017/052863
§ 371 (c)(1),
(2) Date: Mar. 22, 2019

(87) PCT Pub. No.: WO2018/057834
PCT Pub. Date: Mar. 29, 2018

(65) Prior Publication Data
US 2019/0247397 A1 Aug. 15, 2019

Related U.S. Application Data

(60) Provisional application No. 62/398,634, filed on Sep. 23, 2016.

(51) Int. Cl.
| | | |
|---|---|---|
| *A61K 31/517* | (2006.01) | |
| *A61K 31/17* | (2006.01) | |
| *A61K 31/18* | (2006.01) | |
| *A61K 31/416* | (2006.01) | |
| *A61K 31/437* | (2006.01) | |
| *A61K 31/4706* | (2006.01) | |
| *A61K 31/502* | (2006.01) | |
| *A61K 31/5025* | (2006.01) | |
| *A61K 31/519* | (2006.01) | |
| *A61K 31/675* | (2006.01) | |
| *A61K 35/00* | (2006.01) | |
| *A61K 38/00* | (2006.01) | |
| *A61K 38/55* | (2006.01) | |
| *A61K 45/06* | (2006.01) | |
| *A61P 35/02* | (2006.01) | |

(52) U.S. Cl.
CPC ........... *A61K 31/517* (2013.01); *A61K 31/17* (2013.01); *A61K 31/18* (2013.01); *A61K 31/416* (2013.01); *A61K 31/437* (2013.01); *A61K 31/4706* (2013.01); *A61K 31/502* (2013.01); *A61K 31/5025* (2013.01); *A61K 31/519* (2013.01); *A61K 31/675* (2013.01); *A61K 35/00* (2013.01); *A61K 38/005* (2013.01); *A61K 38/55* (2013.01); *A61K 45/06* (2013.01); *A61P 35/02* (2018.01)

(58) Field of Classification Search
CPC .............. A61K 31/517; A61K 31/4706; A61K 38/005; A61K 38/55; A61P 35/02; A61P 35/00
See application file for complete search history.

(56) References Cited

U.S. PATENT DOCUMENTS

| | | | |
|---|---|---|---|
| 8,680,107 B2 | 3/2014 | Laiho et al. | |
| 2008/0269259 A1 | 10/2008 | Thompson et al. | |
| 2010/0179155 A1 | 7/2010 | Laiho et al. | |
| 2019/0224209 A1* | 7/2019 | Soong .............. | A61K 39/39558 |

FOREIGN PATENT DOCUMENTS

| | | |
|---|---|---|
| JP | 2011-500655 | 1/2011 |
| WO | WO 2013/192224 | * 12/2013 |
| WO | 2015143293 A1 | 9/2015 |

OTHER PUBLICATIONS

Fong et al., N Engl J Med 2009, 123-34.*
Cecil Textbook of Medicine, 20th Edition, vol. 1, 1996.*
Gura et al. (Science 1997).*
Johnson et al., (British J. of Cancer 2001).*
Bywater, et al., Dysregulation of the basal RNA polymerase transcription apparatus in cancer. Nat. Rev. Cancer 2013;13:299-314.
Chang, et al., Acyl-coenzyme A:cholesterol acyltransferases. Am J Physiol Endocrinol Metab. 2009; 297(1):E1-9.
Chou, Drug combination studies and their synergy quantification using the Chou-Talalay method. Cancer Res. 2010;70:440-6.
Colis, et al., Design, synthesis and structure-activity relationships of pyridoquinazoline-carboxamides as RNA polymerase I inhibitors. J. Med. Chemistry 2014;57:4950-61.
Drygin, et al., Targeting RNA polymerase I with an oral small molecule CX-5461 inhibits ribosomal RNA synthesis and solid tumor growth. Cancer Res. 2011;71:1418-30.
Drygin, et al., The RNA polymerase I transcription machinery: an emerging target for the treatment of cancer. Annu. Rev. Pharmacol. Toxicol. 2010;50:131-56.
Feng, et al., Chromatin to Clinic: The Molecular Rationale for PARP1 Inhibitor Function. Mol Cell 2015; 58(6):925-34.

(Continued)

*Primary Examiner* — Shobha Kantamneni
(74) *Attorney, Agent, or Firm* — Fish & Richardson P.C.

(57) ABSTRACT

Disclosed herein are compositions comprising a combination of at least one Pol I inhibitor, and at least one autophagy inhibiting compound, and/or at least one ACAT1 inhibiting compound, and/or at least one PARP inhibiting compound and their use in treating cancers and other related neoplastic diseases and which may also include additional chemotherapeutic agents.

8 Claims, 10 Drawing Sheets

(56) References Cited

OTHER PUBLICATIONS

Guetg, et al., Inheritance of silent rDNA chromatin is mediated by PARP1 via noncoding RNA. Mol Cell 2012; 45(6):790-800.
Ikonen, Cellular cholesterol trafficking and compartmentalization. Nat Rev Mol Cell Biol 2008, 9(2):125-38.
Katagiri, et al., The nucleolar protein nucleophosmin is essential for autophagy induced by inhibiting Pol I transcription. Sci Rep. 2015;5:8903.
Kimura, et al., Chloroquine in cancer therapy: a double-edged sword of autophagy. Cancer Res. 2013;73:3-7.
Lee, et al., Inhibitors of acyl-CoA: cholesterol O-acyl transferase (ACAT) as hypocholesterolemic agents. CI-1011: an acyl sulfamate with unique cholesterol-lowering activity in animals fed noncholesterol supplemented diets. J Med Chem. 1996;39(26):5031-4.
Lee, et al., Avasimibe encapsulated in human serum albumin blocks cholesterol esterification for selective cancer treatment. ACS Nano. 2015;9(3):2420-32.
Liu, et al., Regulation of lipid stores and metabolism by lipophagy. Cell Death Differ 2013, 20(1):3-11.
Lord, et al., Mechanisms of resistance to therapies targeting BRCA mutant cancers. Nat Med. 2013; 19(11):1381-8.
Nguyen, et al., Targeting autophagy overcomes Enzalutamide resistance in castration-resistant prostate cancer cells and improves therapeutic response in a xenograft model. Oncogene. 2014;33(36):4521-30.
Peltonen, et al., A targeting modality for destruction of RNA polymerase I that possesses anticancer activity. Cancer Cell 2014;25:77-90.
Yue, et al., Cholesteryl ester accumulation induced by PTEN loss and PI3K/AKT activation underlies human prostate cancer aggressiveness. Cell Metab. 2014;19:393-406.
McAfee, et al., Autophagy inhibitor Lys05 has single-agent antitumor activity and reproduces the phenotype of a genetic autophagy deficiency. Proc Natl Acad Sci U S A. 2012;109(21):8253-8.
Chou, et al., Reversible inhibitor of p97, DBeQ, impairs both ubiquitin-dependent and autophagic protein clearance pathways. Proc Natl Acad Sci U S A. 2011;108(12):4834-9.
Liu, et al., Beclin1 controls the levels of p53 by regulating the deubiquitination activity of USP10 and USP13. Cell 2011;147:223-234.
Egan, et al., Small Molecule Inhibition of the Autophagy Kinase ULK1 and Identification of ULK1 Substrates. Mol Cell. 2015;59(2):285-97.
Chou, et al., Structure-Activity Relationship Study Reveals ML240 and ML241 as Potent and Selective Inhibitors of p97 ATPase. ChemMedChem 2013;8:297-312.
Kitayama, et al., Importance of acyl-coenzyme A:cholesterol acyltransferase ½ dual inhibition for anti-atherosclerotic potency of pactimibe. Eur J Pharmacol 2006;540:121-130.
Ikenoya, et al., A selective ACAT-1 inhibitor, K-604, suppresses fatty streak lesions in fat-fed hamsters without affecting plasma cholesterol levels. Atherosclerosis. 2007; 191(2):290-7.
Netherland, et al., Rimonabant is a dual inhibitor of acyl CoA:cholesterol acyltransferases 1 and 2. Biochem Biophys Res Commun. 2010;398(4):671-6.
Ohshiro, et al., The selectivity of beauveriolide derivatives in inhibition toward the two isozymes of acyl-CoA: cholesterol acyltransferase. Chem Pharm Bull (Tokyo). 2009;57(4):377-81.
Lopez-Farre, et al., Inhibition of acyl-CoA cholesterol acyltransferase by F12511 (Eflucimibe): could it be a new antiatherosclerotic therapeutic? Cardiovasc Ther. 2008;26(1):65-74.
European Search Report in European Appln. No. 17853955.7, dated Mar. 10, 2020, 7 pages.
Fong et al., Inhibition of Poly(ADP-Ribose) Polymerase in Tumors from BRCA Mutation Carriers, N Engl J Med 2009, 123-34.
White et al., "The role for autophagy in cancer," J. Clinc. Invest, 2015, 125:42-46.
Boamah et al., "Poly(ADP-Ribose) polymerase 1 (PARP-1) regulates ribosomal biogenesis in *Drosophila nucleoli*," PLoS Genet., Jan. 2012, 8(1):e1002442, 15 Pages.
Bruno et al., "The primary mechanism of cytotoxicity of the chemotherapeutic agent CX-5461 is topoisomerase II poisoning," Proc. Natl. Acad. Sci. USA, Feb. 2020, 117:8:4053-4060.
Burger et al., "Chemotherapeutic drugs inhibit ribosome biogenesis at various levels," J. Biol. Chem., Apr. 2010, 285:16:12416-25.
International Preliminary Report on Patentability in Appln. No. PCTUS2017/052863, dated Mar. 26, 2019, 5 pages.
International Search Report and Written Opinion in Appln. No. PCT US2017/052863, dated Dec. 28, 2017, 7 pages.
Jaaks et al., "Effective drug combinations in breast, colon and pancreatic cancer cells," Nat, Mar. 2022, 603:7899:166-173.
Kimura et al., "Chloroquine in cancer therapy: a double-edged sword of autophagy," Cancer Res., Jan. 2013, 1:73:1:3-7.
Low et al., "Caveolae-Associated Molecules, Tumor Stroma, and Cancer Drug Resistance: Current Findings and Future Perspectives," Cancers (Basel), Jan. 2022, 25:14(3):589.
Menden et al., "Community assessment to advance computational prediction of cancer drug combinations in a pharmacogenomic screen," Nat Commun. Jun. 17, 2019;10(1):2674.
Palmer et al., "Combination Cancer Therapy Can Confer Benefit via Patient-to-Patient Variability without Drug Additivity or Synergy," Cell. Dec. 14, 2017;171(7):1678-1691.e13.

* cited by examiner

FIG. 1B   FIG. 1C

COMBINATORY TREATMENT STRATEGIES OF CANCER BASED ON RNA POLYMERASE I INHIBITION

CROSS-REFERENCE TO RELATED APPLICATIONS

This application is a 35 U.S.C. § 371 U.S. national entry of International Application PCT/US2017/052863, having an international filing date of Sep. 22, 2017, which claims the benefit of U.S. Provisional Application No. 62/398,634, filed Sep. 23, 2016, the content of each of the aforementioned applications is herein incorporated by reference in their entirety.

STATEMENT OF GOVERNMENTAL INTEREST

This invention was made with government support under grant no. R21 CA193637-01, awarded by the National Institutes of Health. The government has certain rights in the invention.

BACKGROUND OF THE INVENTION

Ribosomal (r) DNA is the most highly transcribed genomic region of the human genome and occurs in a dedicated subcellular compartment, the nucleolus. Transcription of rRNA is mediated by RNA polymerase I (Pol I) that transcribes the multicopy rDNA gene to a long 47S rRNA precursor. The 47S rRNA precursor is processed through multiple steps to the 18S, 5.8S and 28S mature rRNAs requisite for the assembly of the ribosomes. Pol I transcription is initiated by binding of a multisubunit pre-initiation complex to rDNA promoter, which stochastically recruits the Pol I holocomplex. The Pol I holocomplex is composed of 14 subunits in eukaryotes, of which the subunits RPA194, RPA135 and RPA12 form the catalytically active site. Destabilization of the rDNA helix, or loss of the protein framework, will effectively stall transcription. The rate of rRNA transcription is tightly controlled by external signaling pathways that cause the assembly and binding of the preinitiation complex, Deregulation of rRNA synthesis is highly frequent in human cancers. This is due to activation of extracellular and intracellular signaling pathways and oncogenes such as Myc. Conversely, loss-of-function of tumor suppressors p53, pRB, ARF and PTEN lead to activation of Pol I transcription.

Pol I transcription is a rate-limiting step in ribosome biogenesis, a process which is metabolically demanding and on which cells invest significant amounts of energy sources. Pol I transcription is highly responsive to external stimuli and abundantly deregulated in cancer. Yet, attempts to exploit Pol I as a clinically relevant target have been limited and relevant intervention modalities are scarce. In part, this results from lack of knowledge of Pol I regulation and how its inhibition affects other cellular pathways. The mechanisms by which inhibition of Pol I blocks cancer cell growth are not fully understood. There is limited knowledge how inhibition of Pol I intersects with other cancer cell intrinsic deficiencies or drugs.

SUMMARY OF THE INVENTION

The present inventors earlier presented the discovery of an anticancer small molecule, 12H-Benzo[g]pyrido[2,1-b]quinazoline-4-carboxamide, N-[2(dimethylamino)ethyl]-12-oxo (BMH-21) with a distinct mode of inhibition of Pol I (U.S. Pat. No. 8,680,107, issued Mar. 25, 2014), and incorporated by reference herein (FIG. 1). The inventors previously demonstrated that BMH-21 intercalates with GC-rich rDNA, inhibits Pol I and causes proteasome-mediated degradation of RPA194. BMH-21 also showed broad and potent anticancer activity in NCI60 cancer cell lines and reduced tumor burden in mouse xenograft assays. These studies provided proof-of-principle confirmation that Pol I targeting is a feasible approach for cancer control.

Moreover, the present inventors more recently developed a series of BMH-21 variants were prepared and evaluated as potential novel anticancer agents that act via the repression of Pol I activity (International Patent Publication WO2015/143293) and incorporated by reference herein. The activity of BMH-21 is due to its ability to intercalate to GC-rich rDNA sequences, which makes it very different from other 4-ring anthracyclines, which cause DNA damage. Their intercalation modalities are also quite distinct from the anthracyclines intercalating perpendicular to the DNA helix, whereas BMH-21 intercalates in a near-parallel fashion. Notably, all near equipotent derivatives retained a predicted protonation of the terminal amine and had a basic pKa close to that of the parent at 8.6. These findings indicated that the overall charge of the inventive molecules was critical as well as maintaining the length and basic charge close to the end of the carboxamide arm.

In accordance with one or more embodiments, the present invention provides approaches that show unexpected synergistic cancer cell kill by Pol I inhibition and cellular pathways that regulate cellular metabolism. In particular, the present invention describes combination treatment strategies for cancer based on BMH-21 activated pathways and RNA polymerase I inhibition.

In accordance with an embodiment, the present invention provides a composition comprising a compound of formula I:

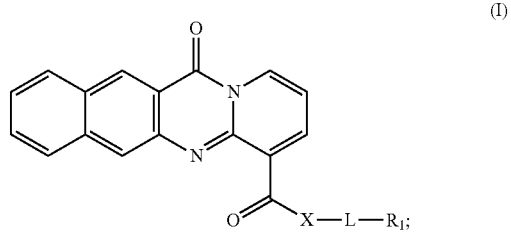

wherein X is $NR_2$;
wherein L is $R_3$ or an optionally substituted cycloamine;

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;

when L is $R_3$, $R_3$ is a straight-chained or branched $C_2$-$C_6$ alkyl group;

when L is $$-N\underset{}{\overset{}{\bigcirc}}Y_m,$$

m=1-8 and each Y is independently selected from $(CH_2)_nY^1_p$ wherein n=1-8, p=0-4 and the sum of n and p is at least 2, and each $Y^1$ is independently selected from $NR_4$, O, S, or P, wherein $R_4$ is as hereinbefore defined for $R_3$, and X≠O; or a pharmaceutically acceptable salt, solvate, stereoisomer, or a prodrug thereof, and an effective amount of at least one or more of the following compounds selected from the group consisting of: an autophagy inhibiting compound; an ACAT1 inhibiting compound; and a PARP inhibiting compound.

In accordance with an embodiment, the present invention provides a pharmaceutical composition comprising a compound of formula I:

(I)

wherein X is $NR_2$;
wherein L is $R_3$ or an optionally substituted cycloamine $$-N\underset{}{\overset{}{\bigcirc}}Y_m;$$

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;

when L is $R_3$, $R_3$ is a straight-chained or branched $C_2$-$C_6$ alkyl group;

when L is $$-N\underset{}{\overset{}{\bigcirc}}Y_m,$$

m=1-8 and each Y is independently selected from $(CH_2)_nY^1_p$ wherein n=1-8, p=0-4 and the sum of n and p is at least 2, and each $Y^1$ is independently selected from $NR_4$, O, S, or P, wherein $R_4$ is as hereinbefore defined for $R_3$, and X≠O; or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound.

In accordance with another embodiment, the present invention provides a composition comprising compounds of formula II, (II)

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein $R_3$ and $R_4$, are independently selected from the group including H, $C_1$-$C_6$ alkyl, and $C_1$-$C_4$ alkoxyl alkyl, having at least one chiral carbon, when $R_2$ is substituted with at least one $NR_3R_4$ group, or a pharmaceutically acceptable salt, solvate, stereoisomer, or a prodrug thereof, and an effective amount of at least one or more of the following compounds selected from the group consisting of: an autophagy inhibiting compound; an ACAT1 inhibiting compound; and a PARP inhibiting compound.

In accordance with a further embodiment, the present invention provides a pharmaceutical composition comprising compounds of formula II,

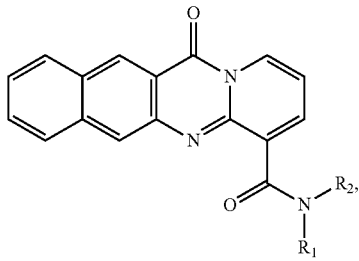

(II)

wherein R₁=H and R₂=C₁-C₆ alkyl, substituted with one or more C₁-C₄ alkyl, OH, NH₂, NR₃R₄, cyano, SO₂R₃, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein R₃ and R₄, are independently selected from the group including H, C₁-C₆ alkyl, and C₁-C₄ alkoxyl alkyl, having at least one chiral carbon, when R₂ is substituted with at least one NR₃R₄ group, or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound.

In accordance with yet another embodiment, the present invention provides a composition comprising at least one of the compounds selected from the group consisting of:

compound 1 (LI-361)

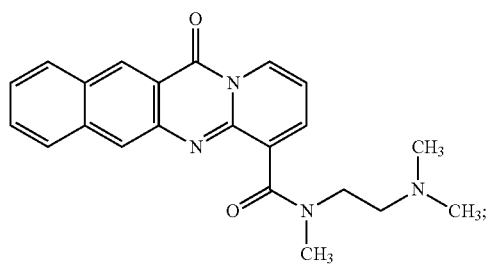

compound 2 (LI-326)

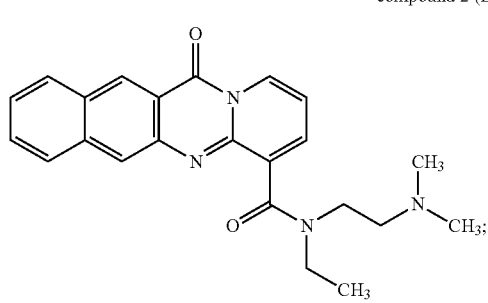

compound 3 (LI-279)

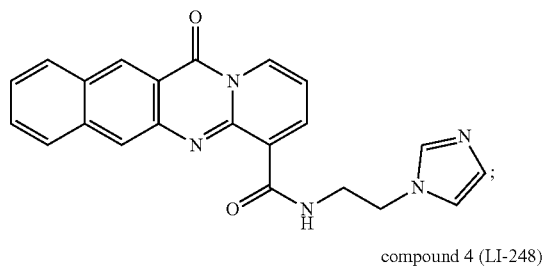

compound 4 (LI-248)

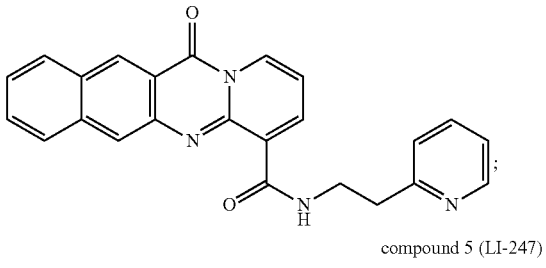

compound 5 (LI-247)

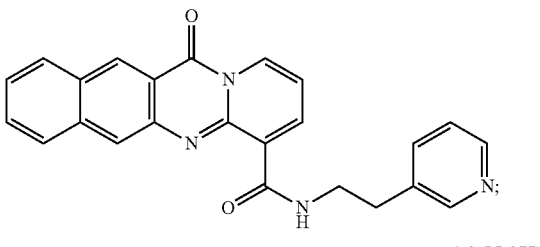

compound 6 (LI-277)

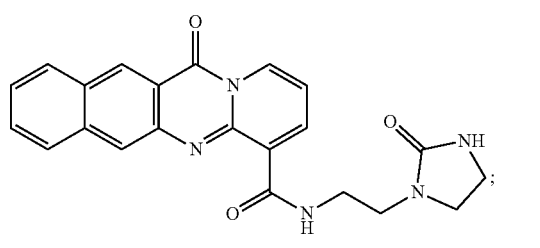

compound 7 (LI-282)

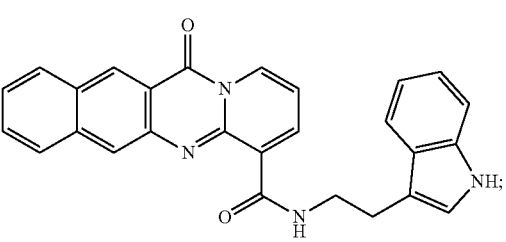

compound 8 (LI-287)

compound 9 (LI-220)
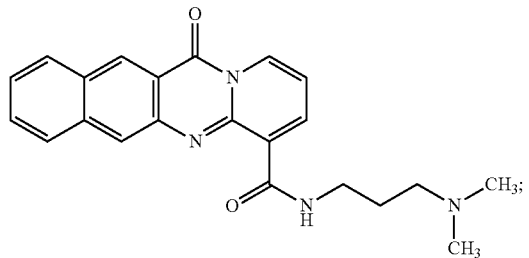
compound 10 (LI-280)
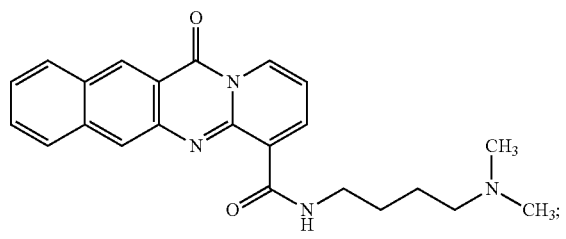
compound 11 (LI-281)
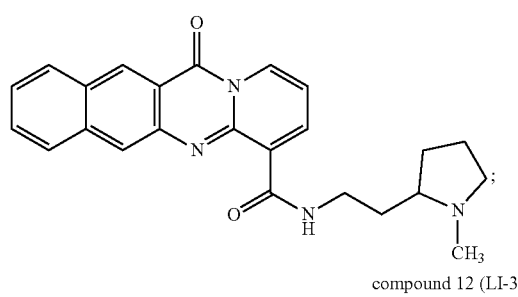
compound 12 (LI-343)
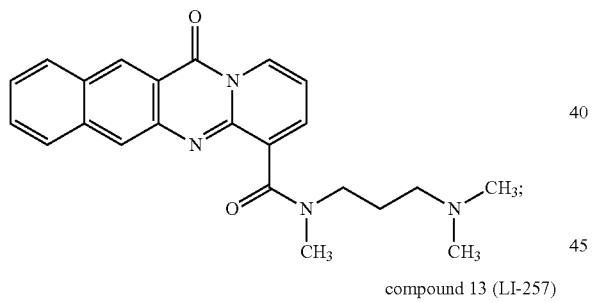
compound 13 (LI-257)
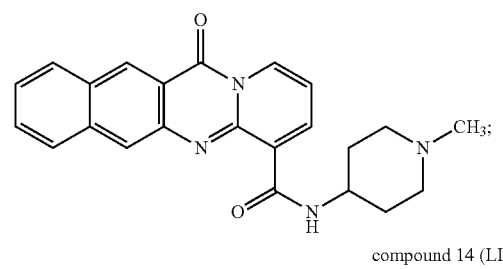
compound 14 (LI-387)
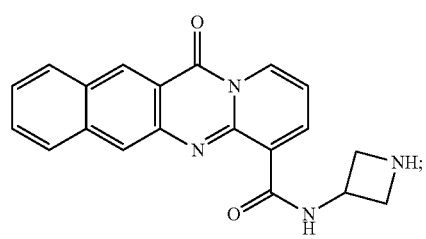
compound 15 (LI-363)
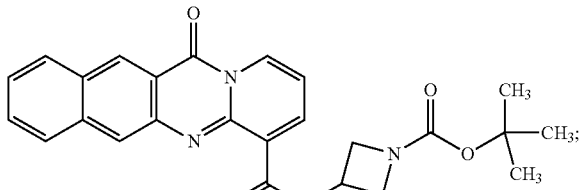
compound 16 (LI-360)
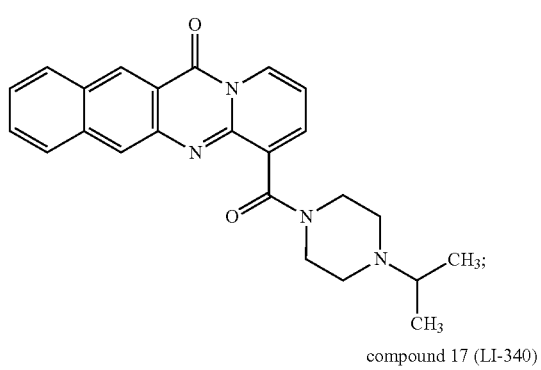
compound 17 (LI-340)
compound 18 (LI-330)
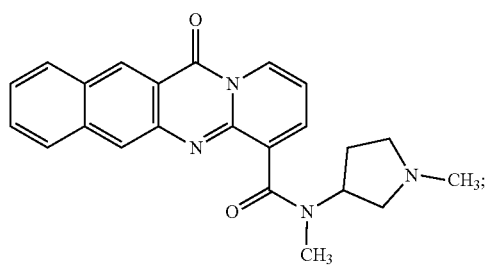
compound 19 (LI-329)
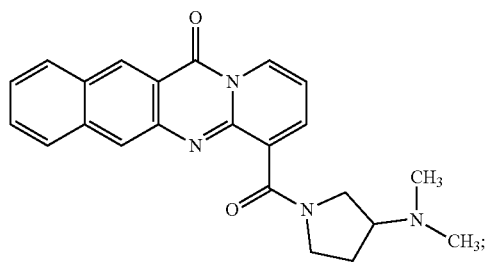

compound 20 (LI-325)
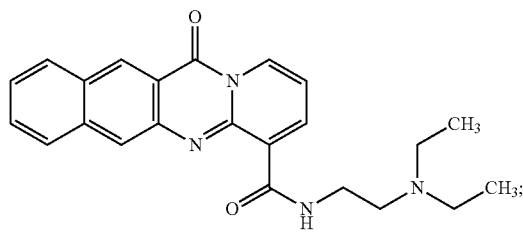
compound 21 (LI-216)
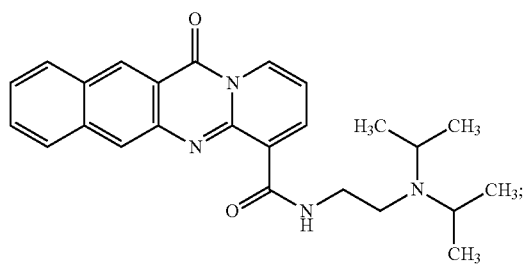
compound 22 (LI-278)
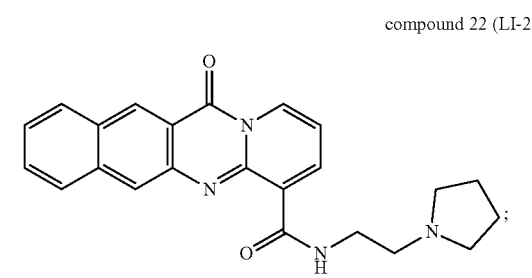
compound 23 (LI-218)
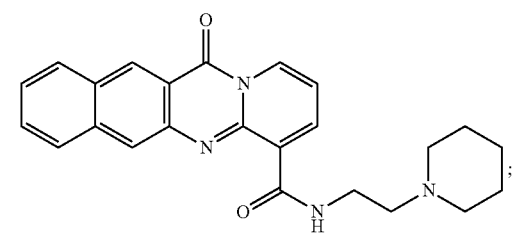
compound 24 (LI-219)
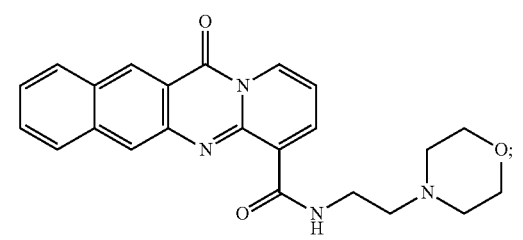
compound 25 (LI-258)
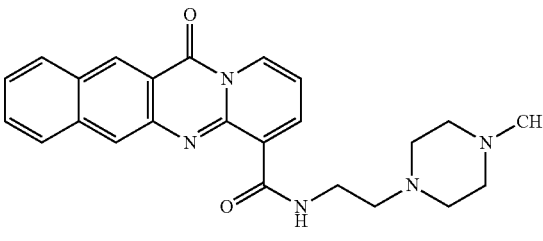
compound 26 (LI-412)
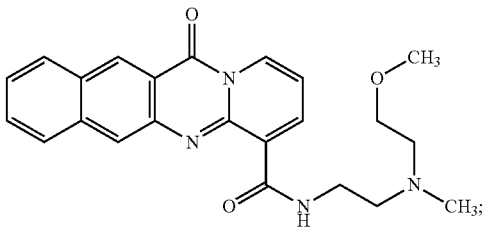
compound 27 (LI-344)
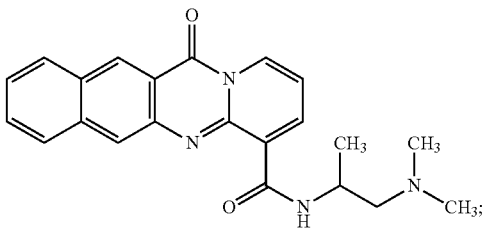
compound 28 (LI-409)
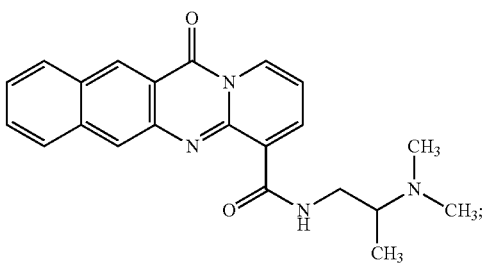
compound 29 (LI-613)
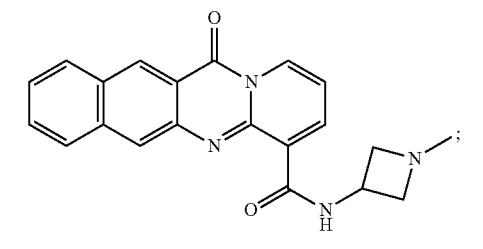
compound 30 (LI-614)
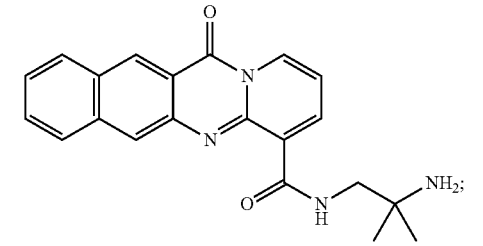
compound 31 (LI-615)
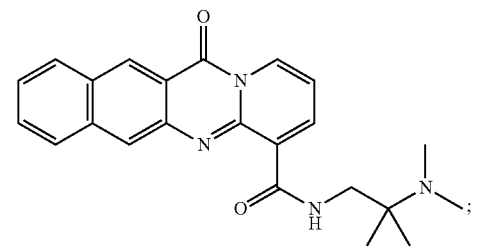

compound 32 (LI-619)

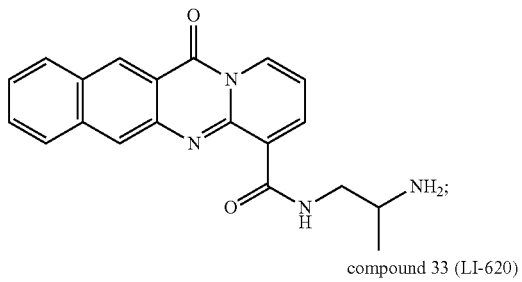

compound 33 (LI-620)

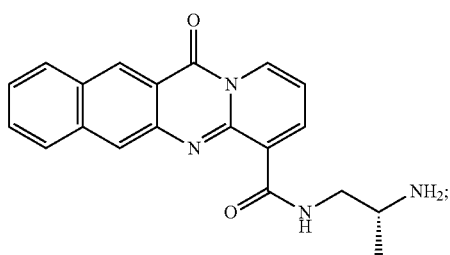

compound 34 (LI-621)

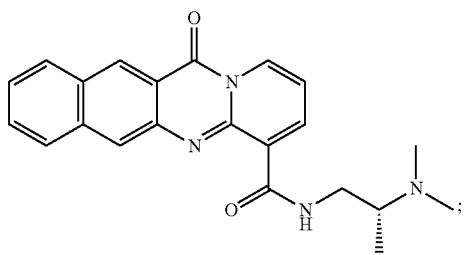

compound 35 (LI-622)

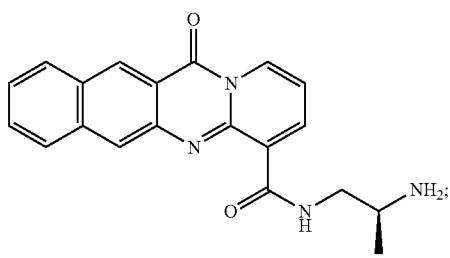

compound 36 (LI-623)

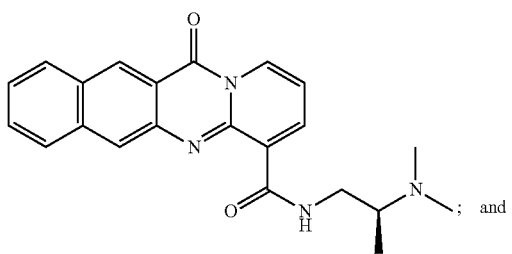

; and compound 37 (LI-246)

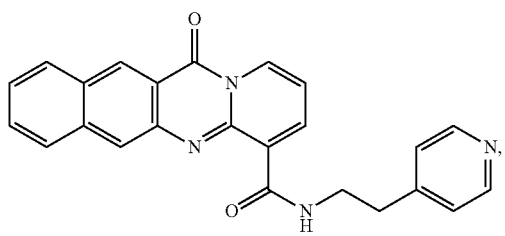

or a pharmaceutically acceptable salt, solvate, stereoisomer, or a prodrug thereof, and an effective amount of at least one or more of the following compounds selected from the group consisting of: an autophagy inhibiting compound; an ACAT1 inhibiting compound; and a PARP inhibiting compound.

In accordance with another embodiment, the present invention provides a pharmaceutical composition comprising at least one of the compounds selected from the group consisting of:

compound 1 (LI-361)

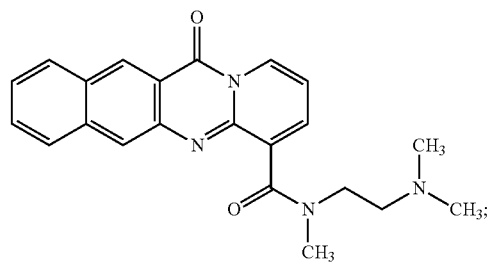

compound 2 (LI-326)

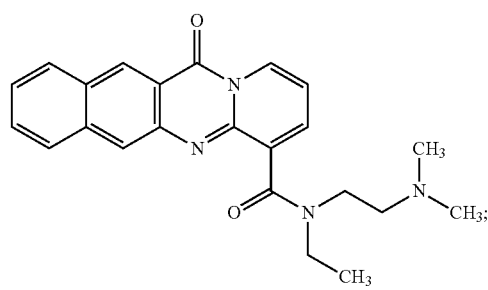

compound 3 (LI-279)

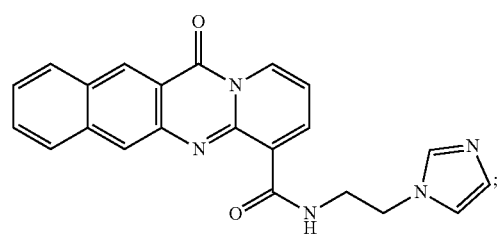

compound 4 (LI-248)
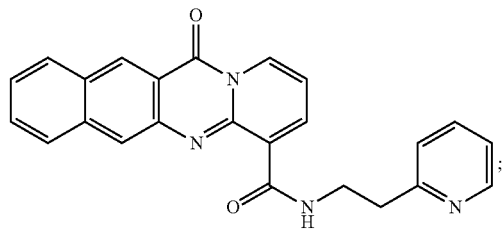
compound 5 (LI-247)
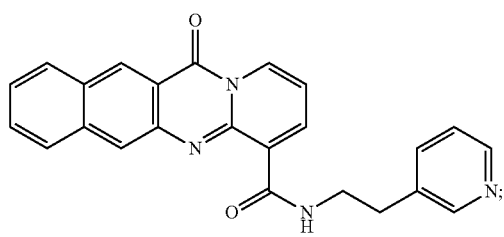
compound 6 (LI-277)
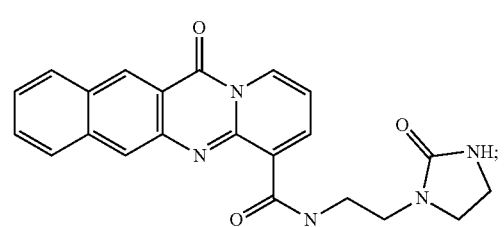
compound 7 (LI-282)
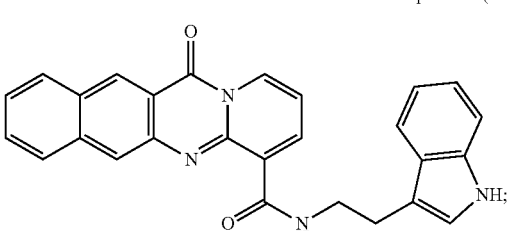
compound 8 (LI-287)
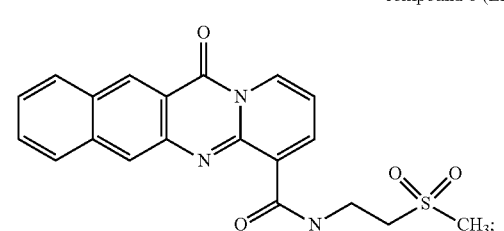
compound 9 (LI-220)
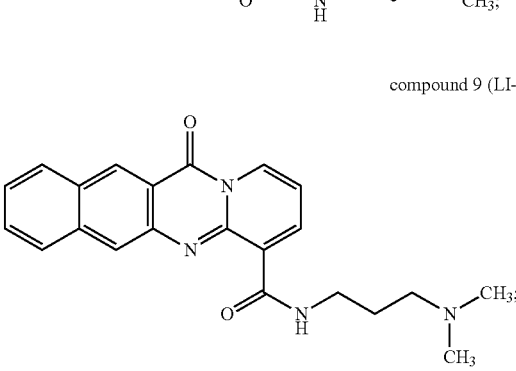
compound 10 (LI-280)
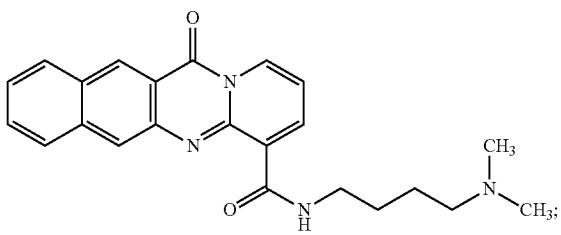
compound 11 (LI-281)
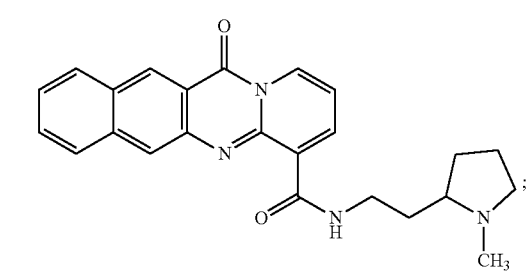
compound 12 (LI-343)
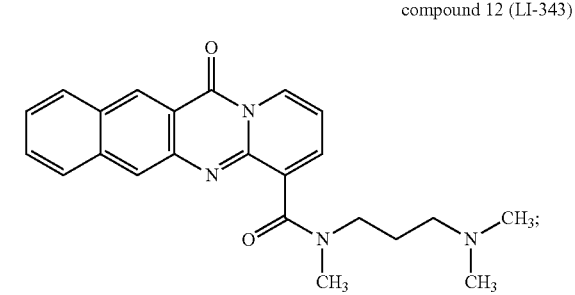
compound 13 (LI-257)
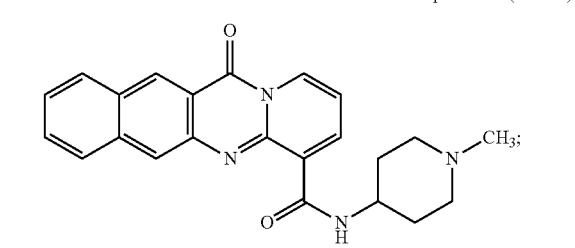
compound 14 (LI-387)
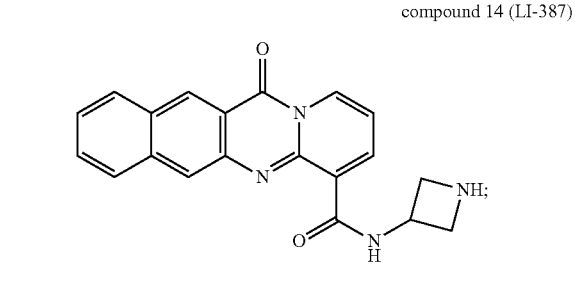
compound 15 (LI-363)
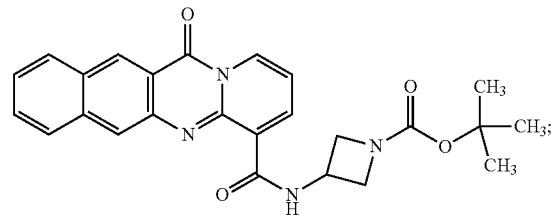

compound 16 (LI-360)
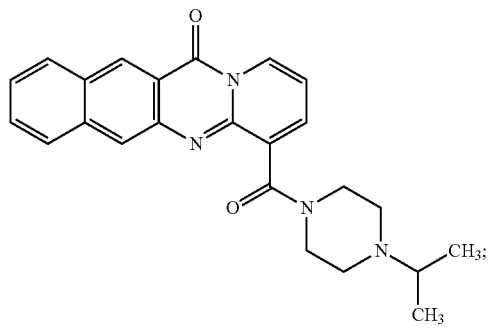
compound 17 (LI-340)
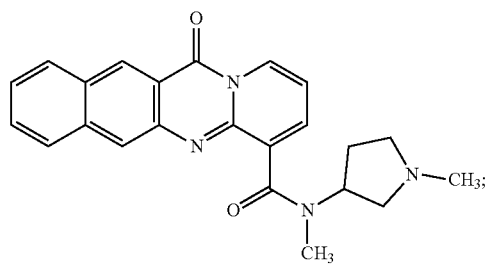
compound 18 (LI-330)
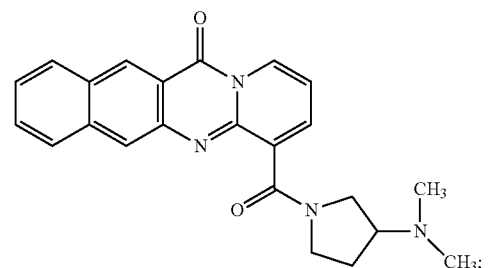
compound 19 (LI-329)
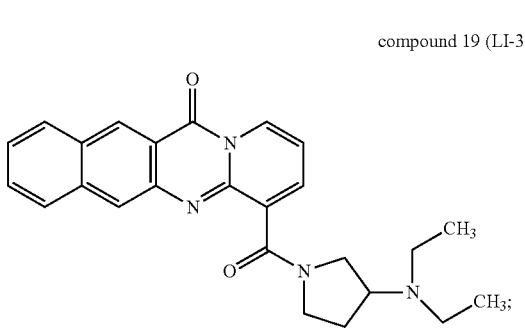
compound 20 (LI-325)
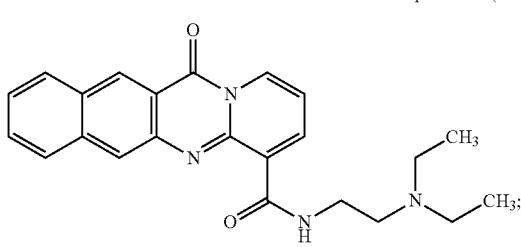
compound 21 (LI-216)
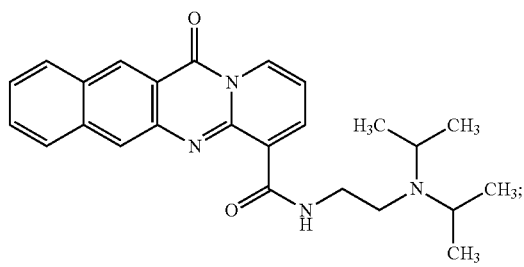
compound 22 (LI-278)
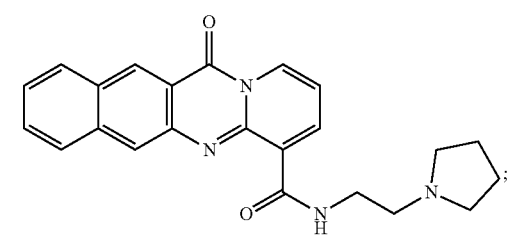
compound 23 (LI-218)
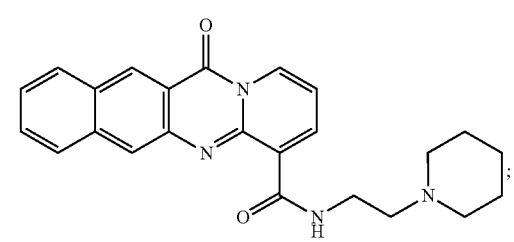
compound 24 (LI-219)
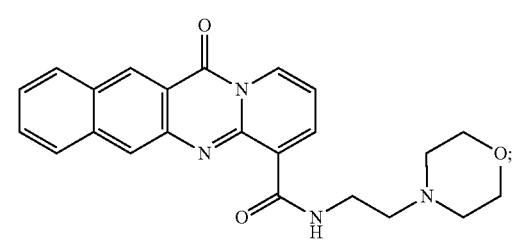
compound 25 (LI-258)
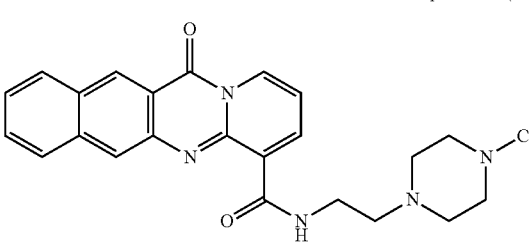
compound 26 (LI-412)
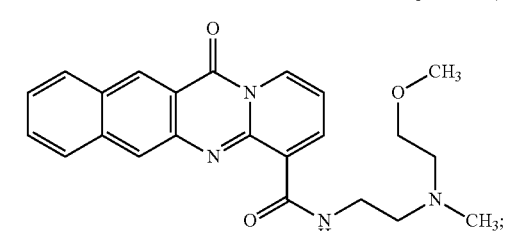

compound 27 (LI-344)

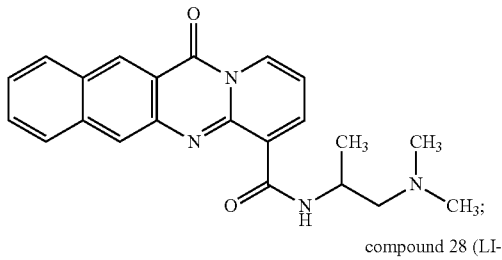

compound 28 (LI-409)

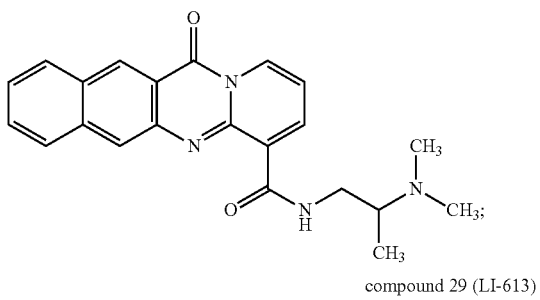

compound 29 (LI-613)

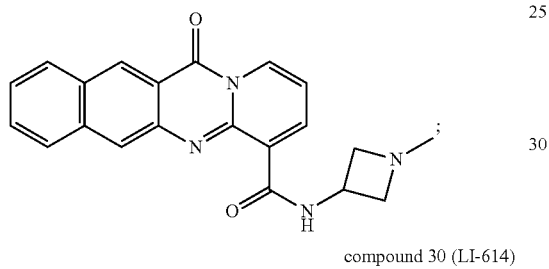

compound 30 (LI-614)

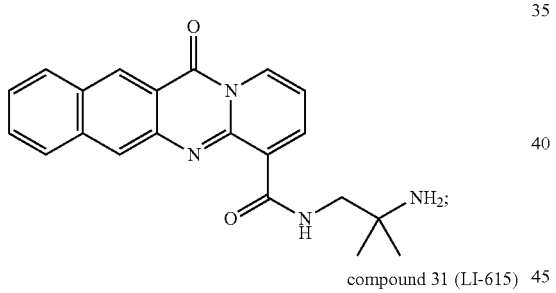

compound 31 (LI-615)

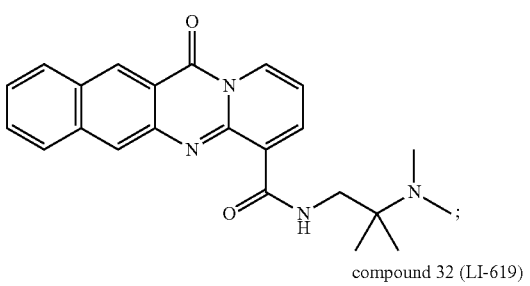

compound 32 (LI-619)

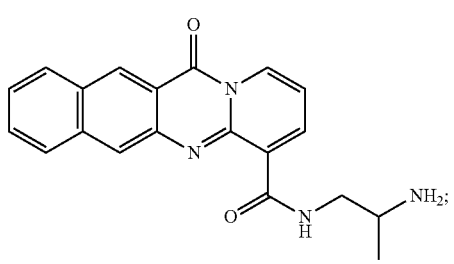

compound 33 (LI-620)

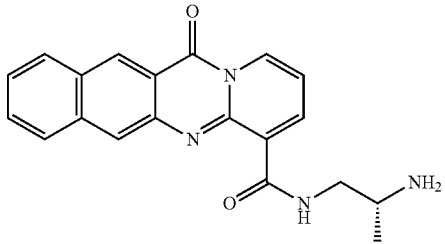

compound 34 (LI-621)

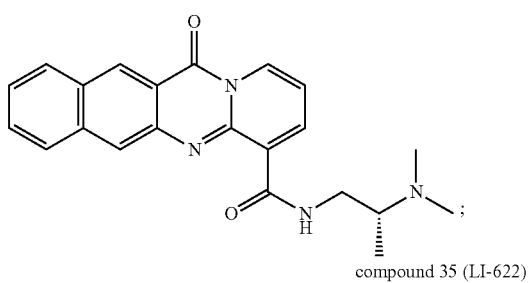

compound 35 (LI-622)

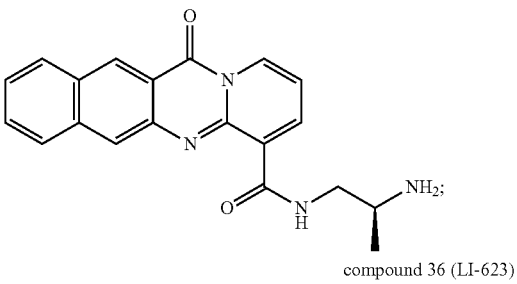

compound 36 (LI-623)

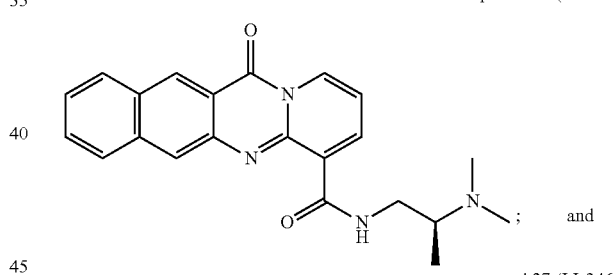

compound 37 (LI-246)

or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound.

In accordance with an embodiment, the present invention provides a method for suppressing or inhibiting the growth of a cancer cell or population of cells comprising contacting the cancer cell or population of cells with an effective amount of a composition comprising the compounds of formula I or formula II, or an analog or derivative thereof, as described herein, and an autophagy inhibiting compound, and/or an ACAT1 inhibiting compound, and/or a PARP inhibiting compound.

In accordance with another embodiment, the present invention provides a method for suppressing or inhibiting the growth of a cancer cell or population of cells comprising contacting the cancer cell or population of cells with an effective amount of a pharmaceutical composition comprising the compounds of formula I or formula II, or an analog or derivative thereof, as described herein, and an autophagy inhibiting compound, and/or an ACAT1 inhibiting compound, and/or a PARP inhibiting compound, and a pharmaceutically acceptable carrier In accordance with an embodiment, the present invention provides a method for treating cancer in a subject comprising administering to the subject an effective amount of a pharmaceutical composition comprising the compounds of formula I or formula II, or an analog or derivative thereof, as described herein, and an autophagy inhibiting compound, and/or an ACAT1 inhibiting compound, and/or a PARP inhibiting compound, and a pharmaceutically acceptable carrier.

In accordance with another embodiment, the present invention provides a method for treating cancer in a subject comprising administering to the subject an effective amount of a pharmaceutical composition comprising the compounds of formula I or formula II, or an analog or derivative thereof, as described herein, and an autophagy inhibiting compound, and/or an ACAT1 inhibiting compound, and/or a PARP inhibiting compound, and at least one additional biologically active agent, and a pharmaceutically acceptable carrier.

BRIEF DESCRIPTION OF THE DRAWINGS

FIGS. 1A-1E illustrate the combinatory activities of BMH-21 with selected drugs. Chou-Talalay combination index (CI) plots for BMH-21. CI<1 denotes synergism, C=1 additive effect, CI≥antagonism. (A) Chemotherapy drugs. (B) Pol I inhibitors. (C) Epigenetic modifiers. 5AZA, 5-aza-2'-deoxycytidine and TSA, trichostatin A. (D) Energy metabolism regulators. Nicotinamide; metformin; 2DG, 2-deoxyglucose; AICAR, AMPK activator 5-Aminoimidazole-4-carboxamide ribonucleotide. (E) Chloroquine. Assays and nomenclature as in (Chou 2010). X-axis, Effect denotes the combinatory drug activity where 1 represents 100% kill.

DETAILED DESCRIPTION OF THE INVENTION

Figure 1A:
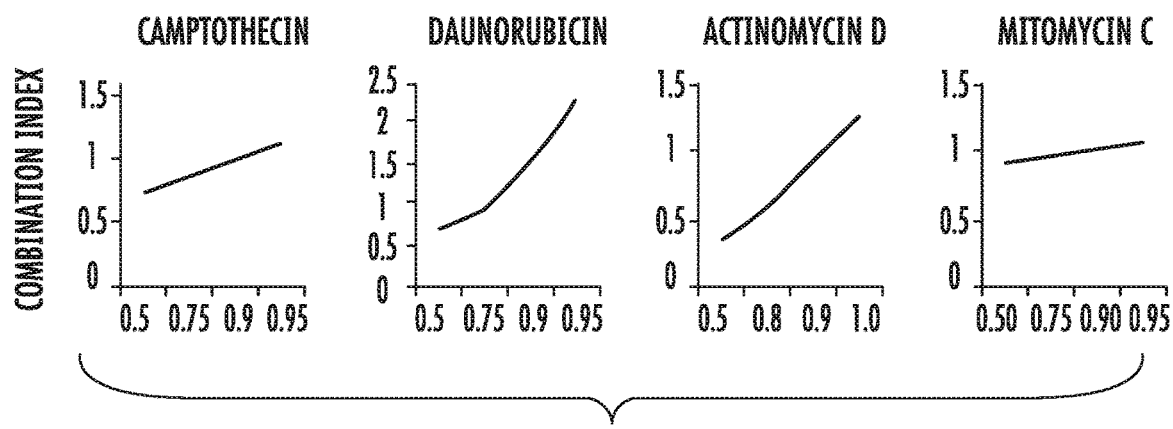
Figure 1D:
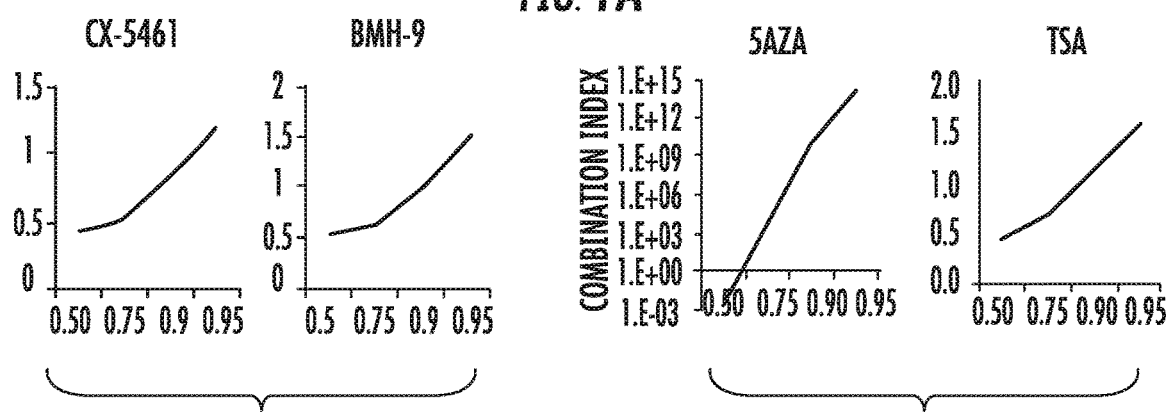
Figure 1D:
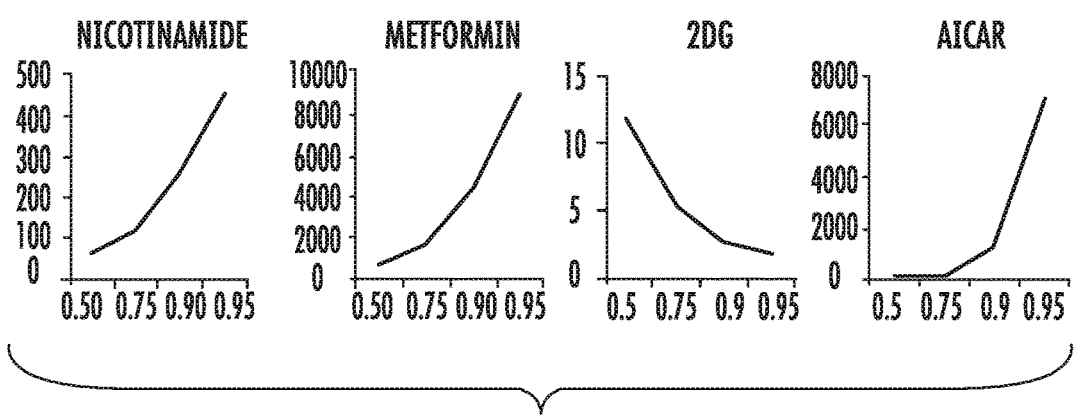
Figure 1E:
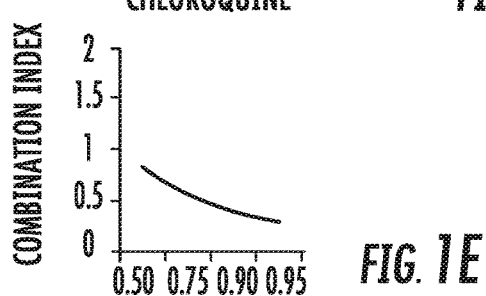

The present inventors previously developed a first-in-class small-molecule cancer therapeutic agent that targets RNA polymerase I (Pol I). Pol I targeting in cancers is highly relevant, because cancer cells are dependent on ribosynthetic activity to support their demands for protein synthesis.

It is thought that tumors may harbor mutations that render them uniquely sensitive to Pol I inhibition. In accordance with one or more embodiments of the present application, a combination of Pol I inhibition with other cancer drugs uniquely provides therapeutic advantages over monotherapy. The synergistic or synthetic lethality which is provided from inhibition of multiple known and unknown effectors of Pol I transcription is potentially advantageous in many cancer types including solid and hematological malignancies, in cancers which have acquired or primary treatment resistances or no current effective treatments.

In accordance with one or more embodiments, the present invention provides approaches that show unexpected synergistic cancer cell killing by Pol I inhibition with the compounds of formula I or formula II, including BMH-21 and with compounds that cellular pathways that regulate cellular metabolism. In particular, the present invention describes combination treatment strategies for cancer based on BMH-21 and related analogs and derivatives on activated pathways and RNA polymerase I inhibition.

The present invention describes numerous combinatory treatment strategies that synergize with Pol I inhibition using the inventors' first-in-class Pol I inhibitor, BMH-21 and the compounds of formula I or formula II, and analogs and derivatives thereof.

While a majority of the tested drugs had either no or antagonistic effects on cancer cell kill with BMH-21, surprisingly, the inventors observed that chloroquine, an antimalarial and autophagy inhibitor, Avasimibe (acyl coenzyme A:cholesterol acyltransferase inhibitor) and poly (ADP)

ribose polymerase (PARP) inhibitors showed strong synergistic cell kill with BMH-21. In one aspect, these findings are advantageous as these compounds are clinically available drugs. The present invention provides the first experimental evidence that links Pol I regulation to pathways regulated by chloroquine, Avasimibe and PARP inhibitors.

As such, the present invention provides compositions and methods comprising combinatory treatments with these drugs that provide therapeutic benefit in the treatment of cancers.

In accordance with an embodiment, the present invention provides a composition comprising a compound of formula I:

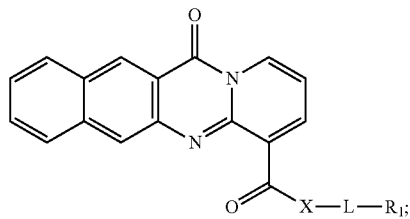

(I)

wherein X is $NR_2$;
wherein L is $R_3$ or an optionally substituted cycloamine

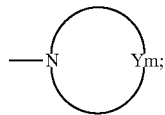

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;

when L is $R_3$, $R_3$ is a straight-chained or branched $C_2$-$C_6$ alkyl group;

when L is

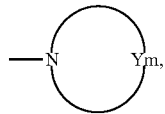

m=1-8 and each Y is independently selected from $(CH_2)_nY^1_p$ wherein n=1-8, p=0-4 and the sum of n and p is at least 2, and each $Y^1$ is independently selected from $NR_4$, O, S, or P, wherein $R_4$ is as hereinbefore defined for $R_3$, and X≠O; or a pharmaceutically acceptable salt, solvate, stereoisomer, or a prodrug thereof, and an effective amount of at least one or more of the following compounds selected from the group consisting of: an autophagy inhibiting compound; an ACAT1 inhibiting compound; and a PARP inhibiting compound.

In accordance with an embodiment, the present invention provides a pharmaceutical composition comprising a compound of formula I:

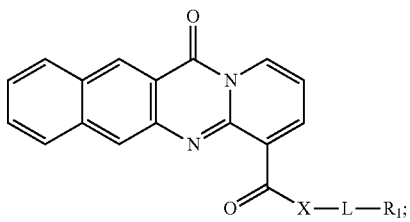

(I)

wherein X is $NR_2$;
wherein L is $R_3$ or an optionally substituted cycloamine

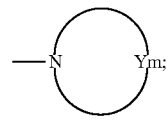

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;

when L is $R_3$, $R_3$ is a straight-chained or branched $C_2$-$C_6$ alkyl group;

when L is

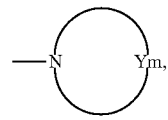

m=1-8 and each Y is independently selected from $(CH_2)_nY^1_p$ wherein n=1-8, p=0-4 and the sum of n and p is at least 2, and each $Y^1$ is independently selected from $NR_4$, O, S, or P, wherein $R_4$ is as hereinbefore defined for $R_3$, and X≠O; or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound.

In accordance with an embodiment, the present invention provides a pharmaceutical composition comprising chirally pure stereoisomer of compound of formula I, wherein L is $R_3$ and $R_3$ is a straight-chained or branched $C_2$-$C_6$ alkyl group having at least one chiral carbon, or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound. In some embodiments, the pharmaceutical composition can further comprise at least one additional biologically active agent.

In accordance with another embodiment, the present invention provides a composition comprising compounds of formula II,

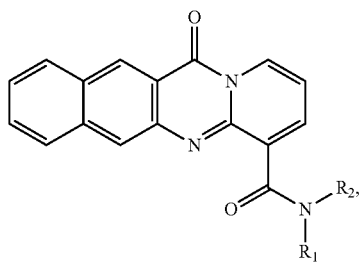

(II)

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein $R_3$ and $R_4$, are independently selected from the group including H, $C_1$-$C_6$ alkyl, and $C_1$-$C_4$ alkoxyl alkyl, having at least one chiral carbon, when $R_2$ is substituted with at least one $NR_3R_4$ group, or a pharmaceutically acceptable salt, solvate, stereoisomer, or a prodrug thereof, and an effective amount of at least one or more of the following compounds selected from the group consisting of: an autophagy inhibiting compound; an ACAT1 inhibiting compound; and a PARP inhibiting compound.

In accordance with a further embodiment, the present invention provides a pharmaceutical composition comprising compounds of formula II,

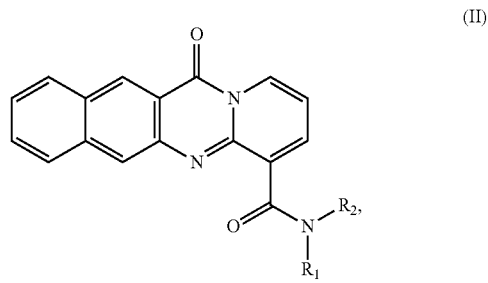

(II)

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein $R_3$ and $R_4$, are independently selected from the group including H, $C_1$-$C_6$ alkyl, and $C_1$-$C_4$ alkoxyl alkyl, having at least one chiral carbon, when $R_2$ is substituted with at least one $NR_3R_4$ group, or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound.

In accordance with a further embodiment, the present invention provides a chirally pure stereoisomer of compound of formula II when $R_2$ is substituted with at least one $NR_3R_4$ group.

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" group mean a group consisting of a sulphur atom bonded to an alkyl-, alkenyl- or alkynyl-group, which is bonded via the sulphur atom to the entity to which the group is bonded.

Included within the compounds of the present invention are the tautomeric forms of the disclosed compounds, isomeric forms including diastereoisomers, and the pharmaceutically-acceptable salts thereof.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)-, and individual isomers are encompassed within the scope of the disclosure. The compounds of the present invention do not include those which are known in art to be too unstable to synthesize and/or isolate. The disclosure is meant to include compounds in racemic and optically pure forms in particular attached to the $R_3$ substituent of compound of Formula I. Optically active (R)- and (S)-, isomers may be prepared using chiral synthons or chiral reagents as disclosed herein, or resolved using conventional techniques. When the compounds described herein contain olefinic bonds or other centers of geometric asymmetry, and unless specified otherwise, it is intended that the compounds include both E and Z geometric isomers.

The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

In accordance with yet another embodiment, the present invention provides a composition comprising at least one of the compounds selected from the group consisting of:

compound 1 (LI-361)

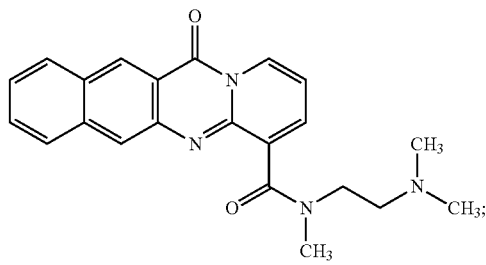

compound 2 (LI-326)

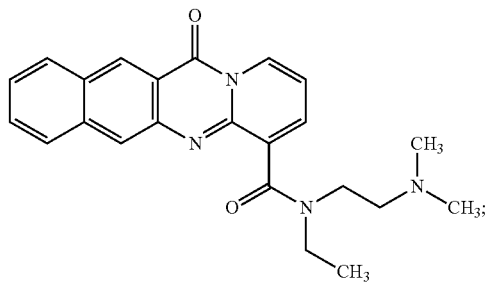

compound 3 (LI-279)

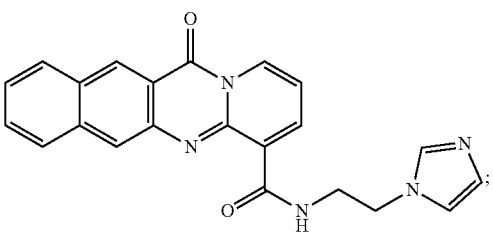

compound 4 (LI-248)

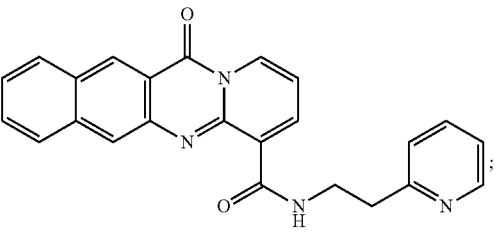

compound 5 (LI-247)

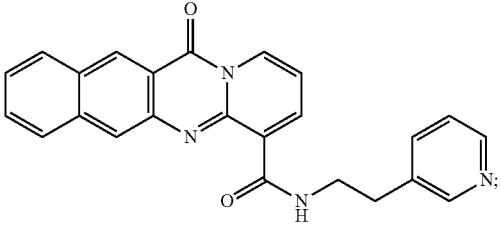

compound 6 (LI-277)
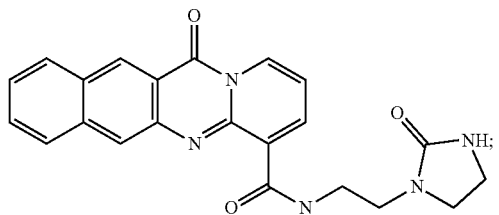
compound 7 (LI-282)
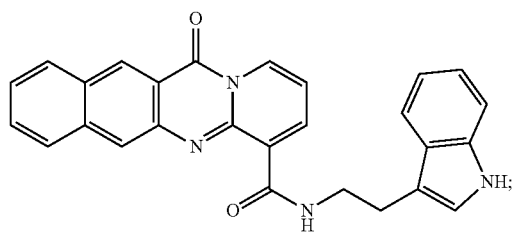
compound 8 (LI-287)
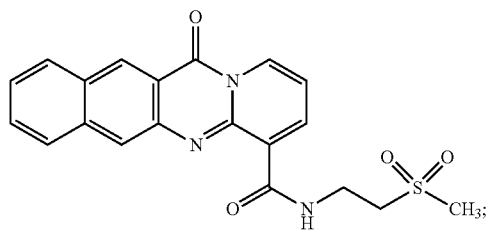
compound 9 (LI-220)
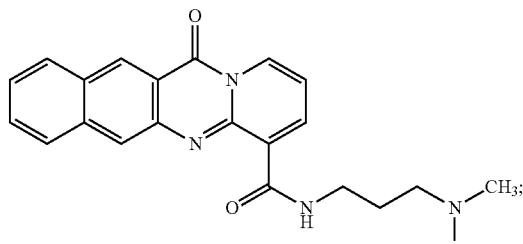
compound 10 (LI-280)
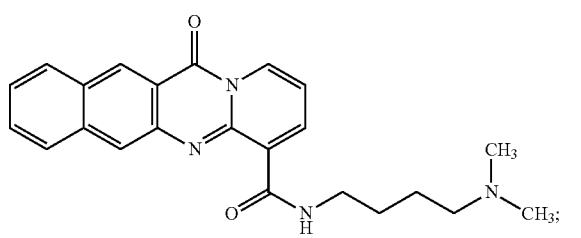
compound 11 (LI-281)
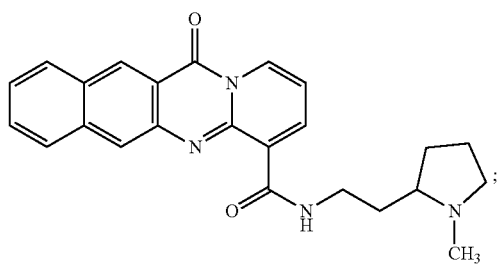
compound 12 (LI-343)
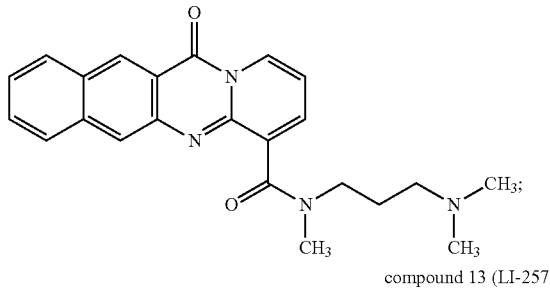
compound 13 (LI-257)
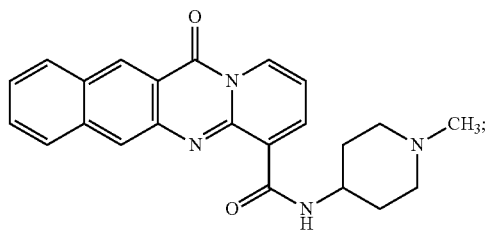
compound 14 (LI-387)
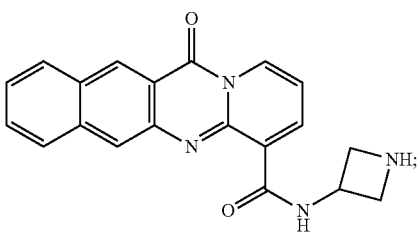
compound 15 (LI-363)
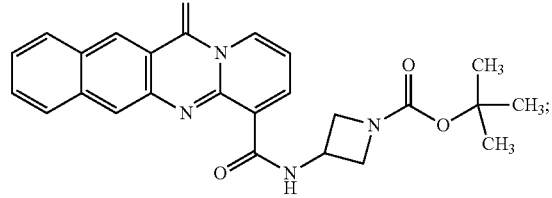
compound 16 (LI-360)
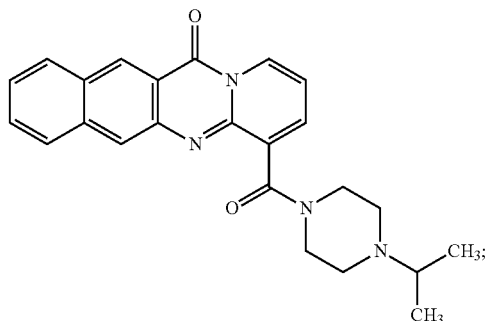

compound 17 (LI-340)
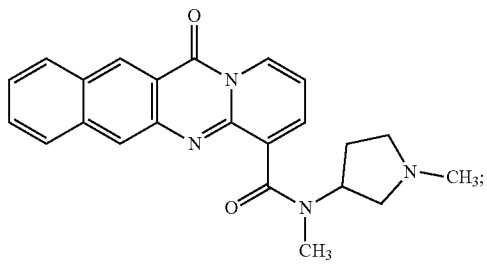
compound 18 (LI-330)
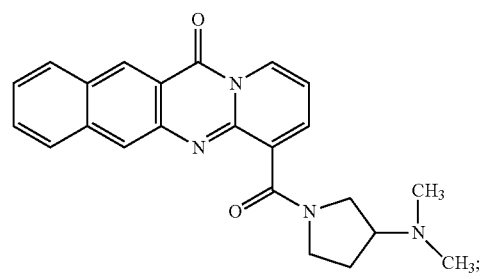
compound 19 (LI-329)
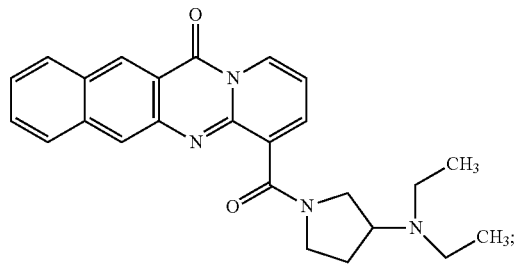
compound 20 (LI-325)
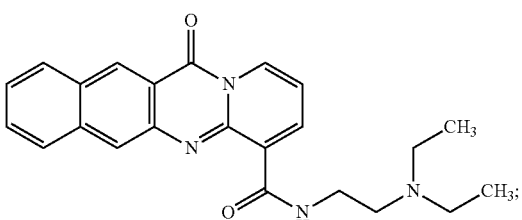
compound 21 (LI-216)
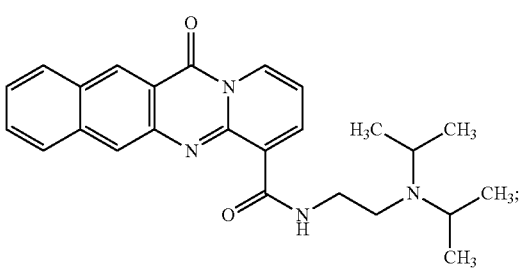
compound 22 (LI-278)
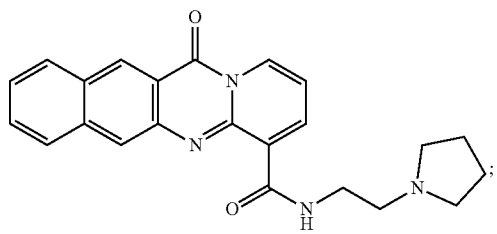
compound 23 (LI-218)
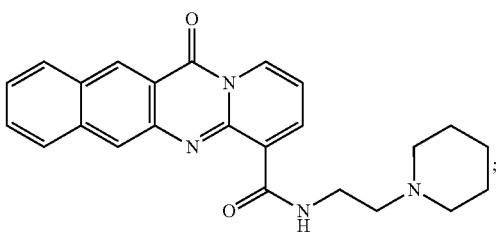
compound 24 (LI-219)
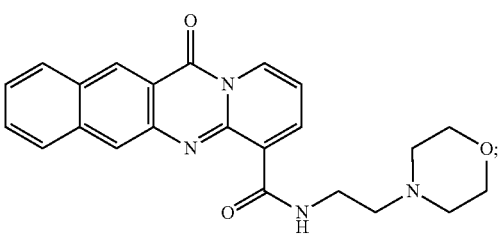
compound 25 (LI-258)
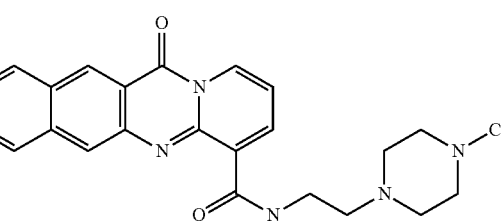
compound 26 (LI-412)
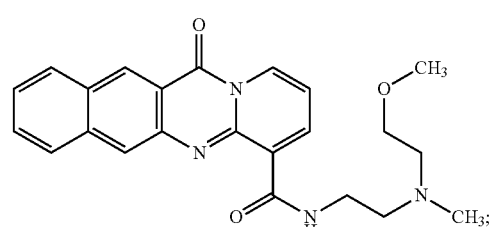
compound 27 (LI-344)
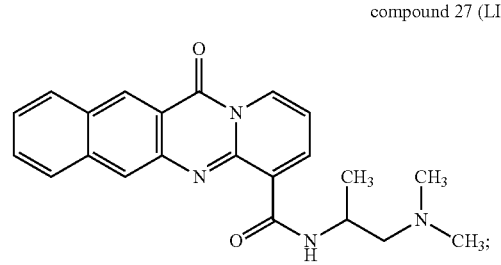

-continued compound 28 (LI-409)

compound 29 (LI-613)

compound 30 (LI-614)

compound 31 (LI-615)

compound 32 (LI-619)

compound 33 (LI-620)

-continued compound 34 (LI-621)

compound 35 (LI-622)

compound 36 (LI-623)

and compound 37 (LI-246)

or a pharmaceutically acceptable salt, solvate, stereoisomer, or a prodrug thereof, and an effective amount of at least one or more of the following compounds selected from the group consisting of: an autophagy inhibiting compound; an ACAT1 inhibiting compound; and a PARP inhibiting compound.

In accordance with another embodiment, the present invention provides a pharmaceutical composition comprising at least one of the compounds selected from the group consisting of:

compound 1 (LI-361)
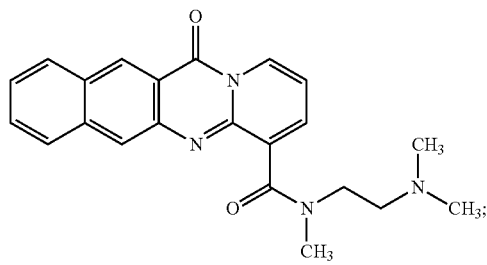
compound 2 (LI-326)
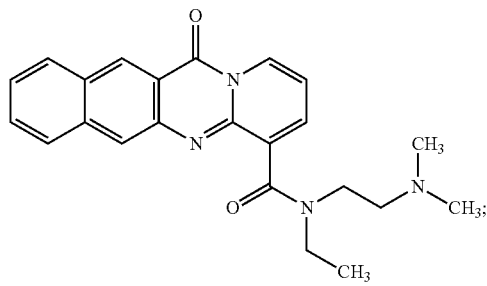
compound 3 (LI-279)
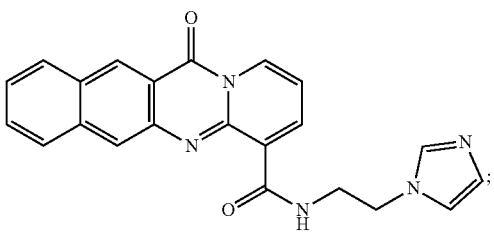
compound 4 (LI-248)
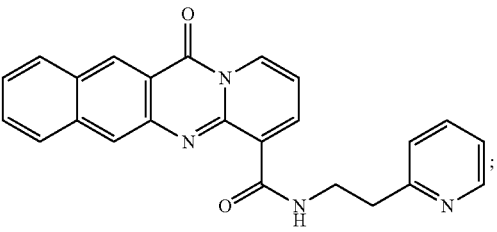
compound 5 (LI-247)
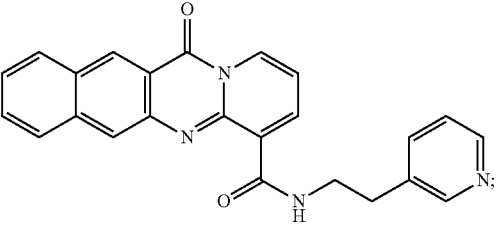
compound 6 (LI-277)
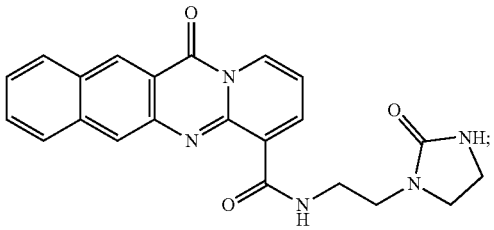
-continued
compound 7 (LI-282)
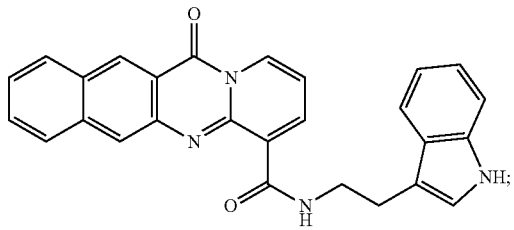
compound 8 (LI-287)
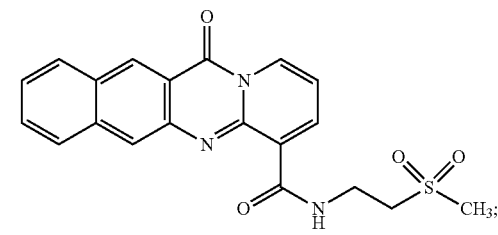
compound 9 (LI-220)
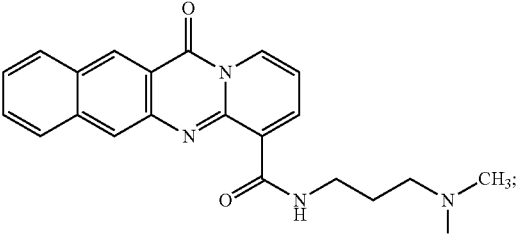
compound 10 (LI-280)
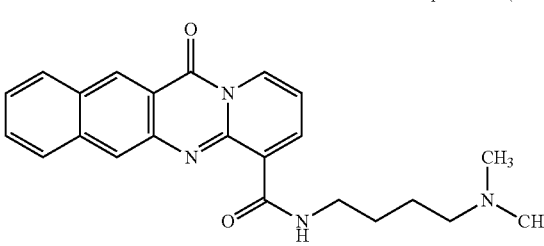
compound 11 (LI-281)
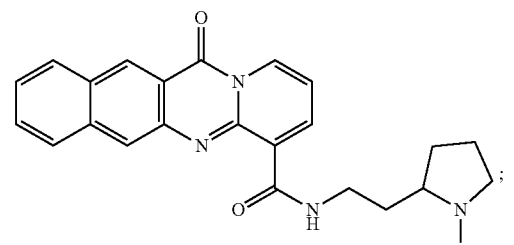
compound 12 (LI-343)
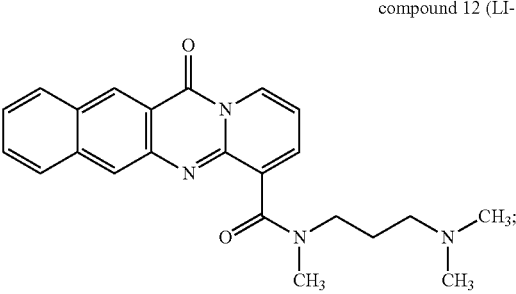

compound 13 (LI-257)
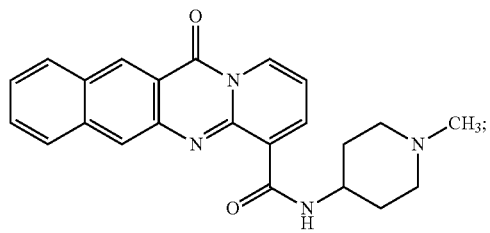
compound 14 (LI-387)
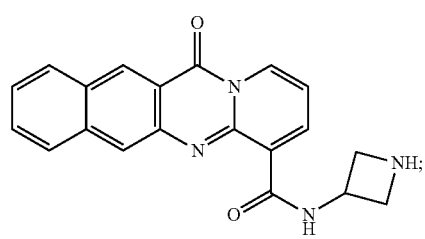
compound 15 (LI-363)
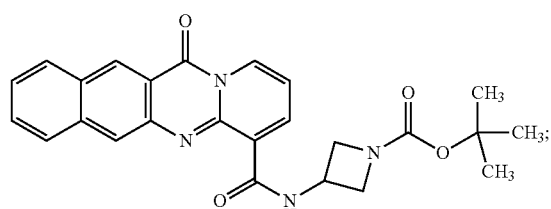
compound 16 (LI-360)
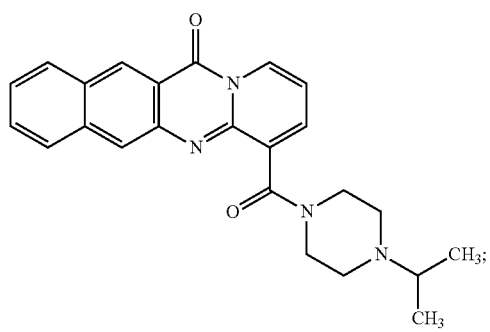
compound 17 (LI-340)
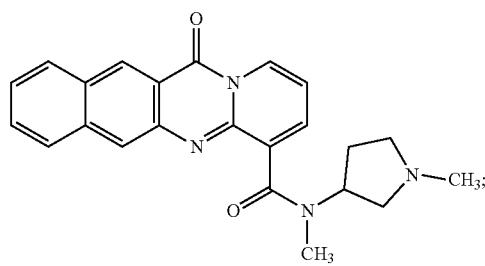
compound 18 (LI-330)
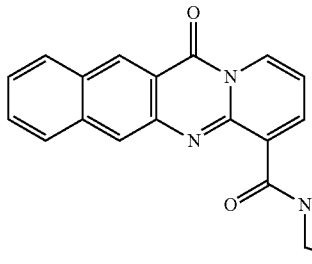
compound 19 (LI-329)
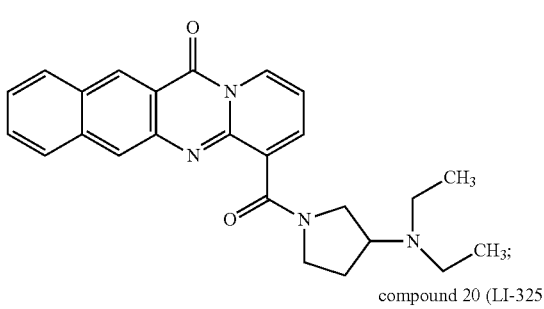
compound 20 (LI-325)
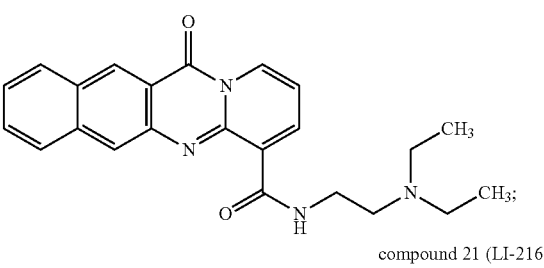
compound 21 (LI-216)
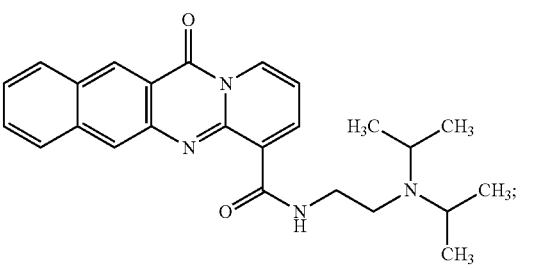
compound 22 (LI-278)
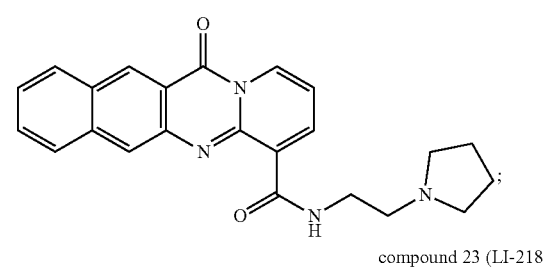
compound 23 (LI-218)
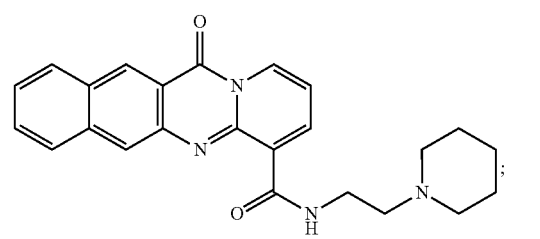

compound 24 (LI-219)
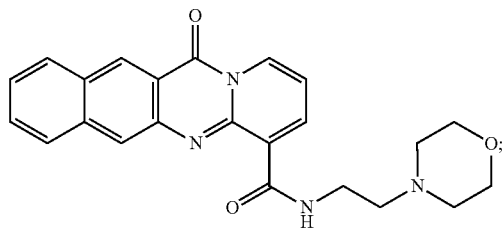
compound 25 (LI-258)
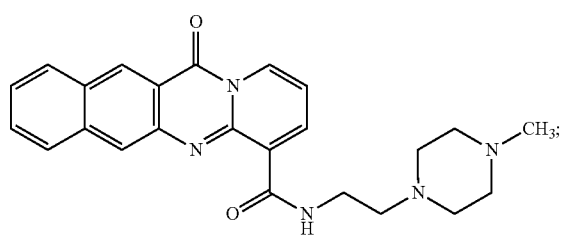
compound 26 (LI-412)
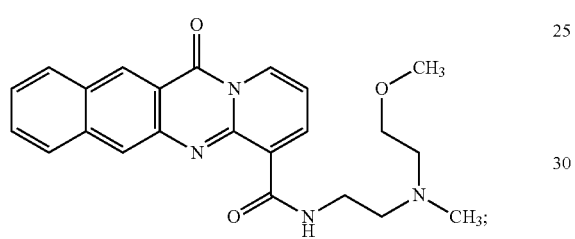
compound 27 (LI-344)
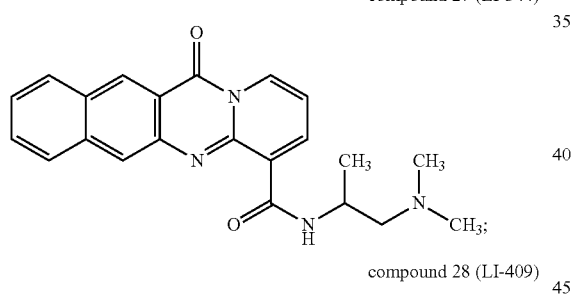
compound 28 (LI-409)
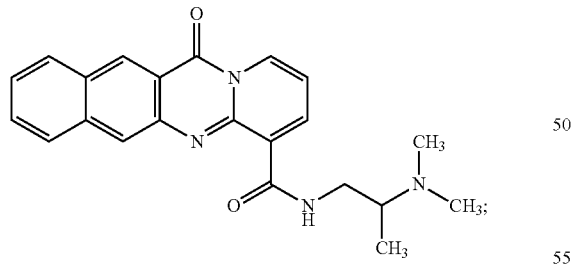
compound 29 (LI-613)
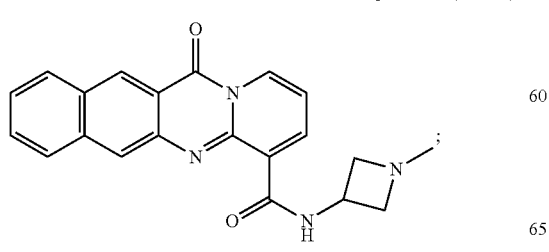
compound 30 (LI-614)
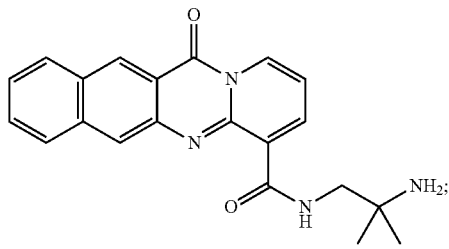
compound 31 (LI-615)
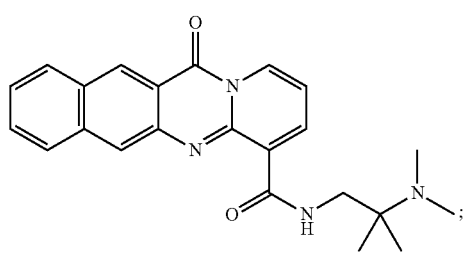
compound 32 (LI-619)
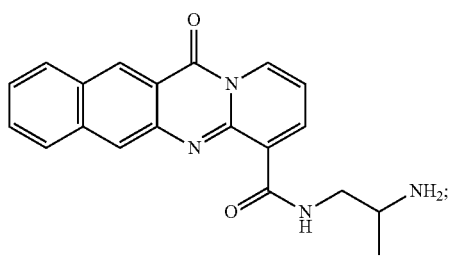
compound 33 (LI-620)
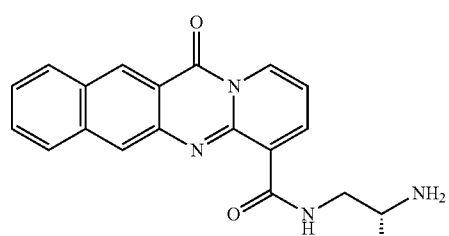
compound 34 (LI-621)
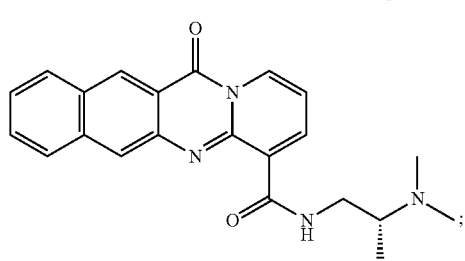

compound 35 (LI-622)

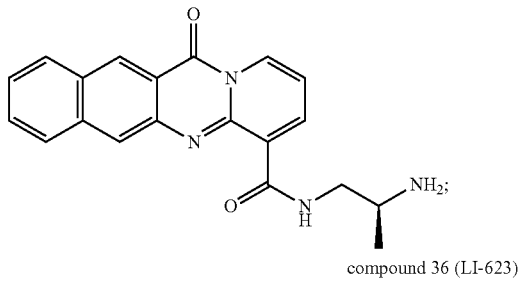

compound 36 (LI-623)

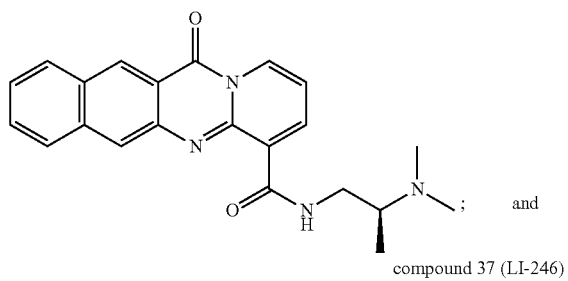
and compound 37 (LI-246)

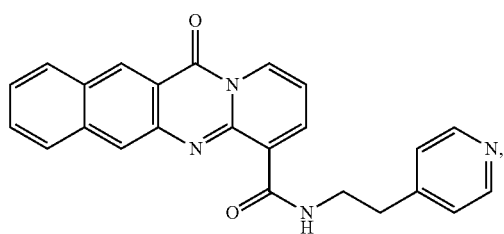

or a pharmaceutically acceptable salt, solvate, stereoisomer, or a prodrug thereof, a pharmaceutically acceptable carrier, and an effective amount of at least one or more of the following compounds selected from the group consisting of: an autophagy inhibiting compound; an ACAT1 inhibiting compound; and a PARP inhibiting compound.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

It is understood by those of ordinary skill, that the compounds of the present invention are inhibitors of RNA polymerase I through one or more mechanisms of action. Without being limited to any particular theory, the compounds of the present invention can inhibit RNA Pol I by intercalation of the nucleic acids at G-C rich regions which block the polymerase activity.

One of ordinary skill in the art understands that p53 is a highly responsive molecule to cellular stress and DNA damage, and implicated in diverse diseases like cancer, ischemia, neuronal disorders, inflammation and also during physiological processes like in normal cellular metabolism, development and aging. Thus, the compounds and compositions of the present invention are useful in prevention or treatment of diseases involving the p53 pathways in conjunction with and an effective amount of an autophagy inhibiting compound and/or and effective amount of an ACAT1 inhibiting compound, and/or an effective amount of a PARP inhibiting compound.

It will be understood by those of ordinary skill in the art, that more than one autophagy inhibiting compound, and/or ACAT1 inhibiting compound and/or PARP inhibiting compound, together or separately, can be included with the Pol I inhibitors disclosed herein. Similarly, combinations of more than one Pol I inhibitor can be used with one or more autophagy inhibiting compounds and/or ACAT1 inhibiting compounds and/or PARP inhibiting compounds in the methods disclosed herein.

In accordance with an embodiment, the present invention provides the use of the compounds or the pharmaceutical compositions disclosed herein in an amount effective for suppressing or inhibiting the growth of a cancer cell or population of cells comprising contacting the cancer cell or population of cells with a compound of formula I, or a pharmaceutically acceptable salt, solvate, stereoisomer, or a prodrug thereof, and an effective amount of an autophagy inhibiting compound and/or and effective amount of an ACAT1 inhibiting compound, and/or an effective amount of a PARP inhibiting compound.

In accordance with an embodiment, the present invention provides a method for suppressing or inhibiting the growth of a cancer cell or population of cells comprising contacting the cancer cell or population of cells with an effective amount of a composition comprising a compound of formula I, or a pharmaceutically acceptable salt, solvate, stereoisomer, or a prodrug thereof, and an effective amount of an autophagy inhibiting compound and/or and effective amount of an ACAT1 inhibiting compound, and/or an effective amount of a PARP inhibiting compound.

In some embodiments, the effective amounts of the compound of formula I and/or autophagy inhibiting compounds and/or ACAT1 inhibiting compounds and/or PARP inhibiting compounds can be synergistic. Thus, in some embodiments methods for use in the treatment of neoplastic diseases and tumors in mammals, for example, can be through the use of synergistically effective amounts of the compounds of formulas I and/or II, in combination with synergistically effective amounts of at least one or more autophagy inhibiting compounds and/or one or more ACAT1 inhibiting compounds and/or one or more PARP inhibiting compounds. In other embodiments, these combinations of compositions can also comprise additional therapeutic or chemotherapeutic agents and pharmaceutically acceptable carriers.

Examples of autophagy inhibiting compounds which can be useful in the inventive methods described herein include, but are not limited to, chloroquine, hydroxychloroquine, lysosomal lumen alkalizers, Lys01, Lys05 and their derivatives (Proc Natl Acad Sci USA. 2012 May 22; 109(21): 8253-8), dimeric forms of hydroxychloroquine (bisaminoquinolines), Bafilomycin A1, vacuolar-type H (+)-ATPases (V-ATPases) ((3Z,5E,7R,8S,9S,11E,13E,15S,16R)-16-[(2S, 3R,4S)-4-[(2R,4R,5S,6R)-2,4-dihydroxy-5-methyl-6-propan-2-yloxan-2-yl]-3-hydroxypentan-2-yl]-8-hydroxy-3,15-dimethoxy-5,7,9,11-tetramethyl-1-oxacyclohexadeca-3,5,11,13-tetraen-2-one), Spautin-1 (6-fluoro-N-[4-fluorobenzyl]quinazolin-4-amine) and derivatives, inhibitor of ubiquitin peptidases and autophagy (Cell. 2011 Sep. 30; 147(1):223-34), SBI-0206965 (2-(5-bromo-2-(3,4,5-trimethoxyphenylamino)pyrimidin-4-yloxy)-N-methylbenzamide), a ULK1 inhibitor (Mol Cell. 2015 Jul. 16; 59(2): 285-97), DBeQ (N2,N4-dibenzylquinazoline-2,4-diamine), a selective p97 ATPase inhibitor; blocks autophagosome maturation (Proc Natl Acad Sci USA. 2011 Mar. 22; 108 (12):4834-9), E 64d ((2S,3S)-trans-epoxysuccinyl-L-leucylamido-3-methylbutane ethyl ester), a cathepsin inhibitor; interferes with autolysosomal digestion, and ML240 (2-(2-Amino-1H-benzo[d]imidazol-1-yl)-N-benzyl-8-methoxyquinazolin-4-amine), an ATP-competitive inhibitor of p97 ATPase; impairs autophagosome maturation (ChemMedChem. 2013 February; 8(2):297-312.) or derivatives of any of the aforementioned compounds having similar activity.

In some embodiments more than one autophagy inhibitor can be combined with one or more Pol I inhibitors disclosed herein. The compounds can be administered together or serially or as a combination of the compounds.

Examples of ACAT (acyl-coenzyme A:cholesterol O-acyltransferase) inhibiting compounds which can be useful in the inventive methods described herein include, but are not limited to, Avasimibe (CI-1011) (ACS Nano. 2015 Mar. 24; 9(3):2420-32) and its derivatives, including avasimin ATR-101 (PD 132301-2, N-[2,6-bis(1-methylethyl)-phenyl]-N'-[[1-[4-(dimethyl-amino)phenyl]cyclopentyl]methyl]urea) (Endocrinology. 2016 May; 157(5): 1775-88), Pactimibe (CS-505) 2-[7-(2,2-dimethylpropanoylamino)-4,6-dimethyl-1-octyl-2,3-dihydroindol-5-yl]acetic acid (Eur J Pharmacol. 2006 Jul. 1; 540(1-3):121-30), K-604 (2-[4-[2-(benzimidazol-2-ylthio)ethyl]piperazin-1yl]-N-[2,4-bis(methylthio)-6-methyl-3-pyridyl]acetamide) (Atherosclerosis. 2007 April; 191(2): 290-7), Rimonabant (5-(4-Chlorophenyl)-1-(2,4-dichlorophenyl)-4-methyl-N-(piperidin-1-yl)-1H-pyrazole-3-carboxamide) (Biochem Biophys Res Commun. 2010 Aug. 6; 398(4):671-6), Beauveriolide and its synthetic derivatives NBV274, 285 and 300 (Chem Pharm Bull (Tokyo). 2009 April; 57(4):377-81), F12511 (eflucimibe, (2S)-2-dodecylsulfanyl-N-(4-hydroxy-2,3,5-trimethylphenyl)-2-phenylacetamide) (Cardiovasc Ther. 2008 Spring; 26(1):65-74), CL-283,546 (N'-heptyl-N-((4-(3-methylbutyl)phenyl)methyl)-N'-(2,4,6-trifluorophenyl)urea), and F-1394 ((1 s,2s)-2-[3-(2,2-Dimethylpropyl)-3-nonylureido]aminocyclohexane-1-yl 3-[N-(2,2,5,5-tetramethyl-1,3-dioxane-4-carbonyl)amino]propionate) or derivatives of any of the aforementioned compounds having similar activity.

In some embodiments more than one ACAT inhibitor can be combined with one or more Pol I inhibitors disclosed herein. The compounds can be administered together or serially or as a combination of the compounds.

Examples of PARP inhibiting compounds which can be useful in the inventive methods described herein include, but are not limited to, olaparib (AZD2811) 4-[[3-[4-(cyclopropanecarbonyl)piperazine-1-carbonyl]-4-fluorophenyl] methyl]-2H-phthalazin-1-one, veliparib (ABT888) 2-[(2R)-2-methylpyrrolidin-2-yl]-1H-benzimidazole-4-carboxamide, rucaparib (AG014699), niraparib (MK4827) 2-[4-[(3 S)-piperidin-3-yl]phenyl]indazole-7-carboxamide, talazoparib (BMN673) 8S,9R)-5-fluoro-8-(4-fluorophenyl)-9-(1-methyl-1H-1,2,4-triazol-5-yl)-8,9-dihydro-2H-pyrido [4,3,2-de]phthalazin-3(7H)-one, CEP-9722 and CEP-8983, and MRL-45696 (niraparib derivative) or derivatives of any of the aforementioned compounds having similar activity.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect.

In one or more aspects, the therapeutic methods of the present invention are useful in the treatment of the disease of cancer and other neoplastic diseases.

More specifically, the pharmaceutical compositions used in the therapeutic treatments of the present invention may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 g, about 1.0-50 μg or about 1.0-20 mg per day for adults (at about 60 kg).

The daily dosage of the pharmaceutical compositions used in the therapeutic treatments of the present invention may be varied over a wide range from about 0.1 ng to about 1000 mg per adult human per day. For oral administration, the compositions may be provided in the form of tablets containing from about 0.1 ng to about 1000 mg of the composition or 0.001, 0.002, 0.003, 0.004, 0.005, 0.01, 0.05, 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions used in the therapeutic treatments of the present invention may be administered on a regimen of about 1 to about 10 times per day.

In the case of injections, it is usually convenient to give by an intravenous route in an amount of about 0.0001 μg-30 mg, about 0.01 μg-20 mg or about 0.01-10 mg per day to adults (at about 60 kg). In the case of other animals, the dose calculated for 60 kg may be administered as well. More specifically, in the case of injections, it is usually convenient to give pharmaceutical compositions by a subcutaneous route in an amount of about 0.01 mg/kg to about 0.5 mg/kg of pharmaceutical compositions, more specifically, about 0.01 mg/kg to 0.5 mg/kg, about 0.02 mg/kg to about 0.5 mg/kg, about 0.03 mg/kg to about 0.5 mg/kg, about 0.04 mg/kg to about 0.45 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on.

Doses of a pharmaceutical compositions used in the therapeutic treatments of the present invention of the present invention can optionally include 0.0001 μg to 1,000 mg/kg/administration, or 0.001 μg to 100.0 mg/kg/administration, from 0.01 μg to 10 mg/kg/administration, from 0.1 μg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml concentration per single or multiple administration or any range, value or fraction thereof.

As a non-limiting example, treatment of subjects can be provided as a one-time or periodic dosage of the compositions used in the therapeutic treatments of the present invention of the present invention are from 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions used in the therapeutic treatments of the present invention may be administered at least once a week over the course of several weeks. In one embodiment, the pharmaceutical compositions are administered at least once a week over several weeks to several months. In another embodiment, the pharmaceutical compositions used in the therapeutic treatments of the present invention are administered once a week over four to eight weeks. In yet another embodiment, the pharmaceutical compositions are administered once a week over four weeks.

More specifically, the pharmaceutical compositions used in the therapeutic treatments of the present invention may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions used in the therapeutic treatments of the present invention may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions used in the therapeutic treatments of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions used in the therapeutic treatments of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions used in the therapeutic treatments of the present invention may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions used in the therapeutic treatments of the present invention may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

As used herein, the term "treat," as well as words stemming therefrom, includes diagnostic and preventative as well as disorder remitative treatment.

It is also contemplated that in an embodiment of the present invention, the methods of treatment disclosed herein are useful against many mammalian tumors, including, for example, breast cancer, prostate cancer, pancreatic cancer, colon cancer, hepatoma, glioblastoma, ovarian cancer, leukemia, Hodgkin's lymphoma and multiple myeloma.

It will be understood by those of ordinary skill in the art that the term "tumor" as used herein means a neoplastic growth which may, or may not be malignant. Additionally, the compositions and methods provided herein are not only useful in the treatment of tumors, but in their micrometastases and their macrometastases. Typically, micrometastasis is a form of metastasis (the spread of a cancer from its original location to other sites in the body) in which the newly formed tumors are identified only by histologic examination; micrometastases are detectable by neither physical exam nor imaging techniques. In contrast, macrometastases are usually large secondary tumors.

In accordance with an embodiment, the present invention provides compositions and methods for the prevention and/or treatment of tumors, and their micrometastases and their macrometastases.

It is contemplated that the therapeutic methods and compositions disclosed herein can also be combined with one or more existing therapeutic, chemotherapeutic agents and regimens.

As used herein, the term "therapeutic agent(s)" encompasses drugs and other active agents, such as chemotherapeutic agents, immunotherapeutic agents, such as, for example, immune checkpoint inhibitors.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

EXAMPLES

Cells and Viability Assay. A375 melanoma and LNCaP prostate cancer cells were from American Type Culture Collection. HCT116 p53+/+ and −/− cells were from Dr. F. Bunz. MR49F cells were from Dr. M. Gleave. Cells were maintained at 37° C. in a humidified atmosphere containing 5% CO2. Cells were plated in 96-well plates at a density of 3,000 cells/well in triplicate and incubated for 48 h with the compounds. Viability was determined using CellTiter-Blue Cell Viability Assay (Promega) according to manufacturer's instructions. Chou-Talaley algorithm (Compusyn) was used to define the combination index (CI) where CI<1 denotes synergism, CI>1 denotes antagonism and CI=1 is additive. Effect denotes the combinatory drug activity where 1 represents 100% kill. Drugs were obtained as follows: chloroquine, actinomycin D, 2-Deoxy-D-glucose, 5-Aza-2'-deoxycytidine, AICAR, bafilomycin A, camptothecin, daunorubicin, Mitomycin C, nicotinamide, and trichostatin A (Sigma), Avasimbe, BMN-673, CX-5461, metformin, and olaparib (SelleckChem). BMH-21 and BMH-9 were as in our published studies.

Immunofluorescence and Epifluorescence Microscopy. Cells grown on coverslips were fixed in 3.5% paraformaldehyde, permeabilized with 0.5% NP-40 and blocked with 3% BSA. Cells were stained for LC3-II and cleaved caspase-3 (Cell Signaling). Alexa 488-conjugated secondary antibodies were from Invitrogen. DNA was counterstained with DAPI (Invitrogen). Images were captured using Axioplan2 fluorescence microscope (Zeiss) equipped with Axio-Cam HRc CCD-camera and AxioVision 4.5 software using EC Plan-Neofluar 20× or 40× objectives (Zeiss).

Immunoblotting. Cells were lysed in 0.5% NP-40 buffer (25 mM Tris-HCl, pH 8.0, 120 mM NaCl, 0.5% NP-40, 4 mM NaF, 100 µM $Na_3VO_4$, 100 KIU/ml aprotinin, 10 µg/ml leupeptin) or RIPA lysis buffer. Proteins were separated on SDS-PAGE, blotted, probed for respective proteins and detected using ECL (Amersham). The primary antibodies used for detection were LC3-II and cleaved caspase-3 (Cell Signaling). HRP-conjugated secondary antibodies were from DAKO or Santa Cruz Biotechnology.

Flow cytometry. Cell cycle distribution and cell death were analyzed with flow cytometry. Cells were harvested and fixed in 70% ethanol at −20° C. followed by RNaseA treatment and stained with propidium iodide. A total of 10,000 counts were collected (LSR, Becton Dickinson). Cells present in sub-G1 population were analyzed using the acquisition software (CellQuest).

Statistical analysis. Statistical analysis was performed by Student's t test. Differences were considered statistically significant at $P<0.05$.

Example 1

The Effects of BMH-21 in Combination with Other Chemotherapeutic Agents.

The inventors tested the combinatory effects of BMH-21 (Peltonen et al., 2014, Colis et al., 2014) on cancer cell viability using a panel of chemotherapeutic agents (topoisomerase poisons [doxorubicin, camptothecin, Actinomycin D, mitomycin C], selective Pol I inhibitors [CX-5461, BMH-9], epigenetic modulators [5-aza-2'-deoxycytidine, trichostatin A], agents and drugs that affect glucose and energy metabolism [2-deoxyglucose, nicotinamide] and chloroquine, an antimalarial and autophagy inhibitor (Kimura et al., 2013) (FIG. 1). The drugs were combined at constant concentrations, applied to cancer cells (A375 human melanoma cells), incubated for 48 hours, and cell viability was determined using Cell TiterBlue viability assay (Promega). The fraction of cell death as compared to the controls was determined. The data was analyzed using Chou-Talalay algorithm (Chou 2010) to define drug combination indices (CI) that demonstrate synergism (CI<1), antagonism (CI>1) and additive effects (CI-1) over a wide range of effect levels in repeated assays. DNA targeting drugs, several metabolic inhibitors, other selective Pol I inhibitors and epigenetic modifiers had strong antagonistic effects with BMH-21 (FIGS. 1A-D). However, a combination of BMH-21 with chloroquine showed strongly synergistic activity (FIG. 1E). More detailed assessment of this synergy is shown below.

Example 2

The Combinatory Effect of BMH-21 and Autophagy Inhibitors.

Figure 2A:
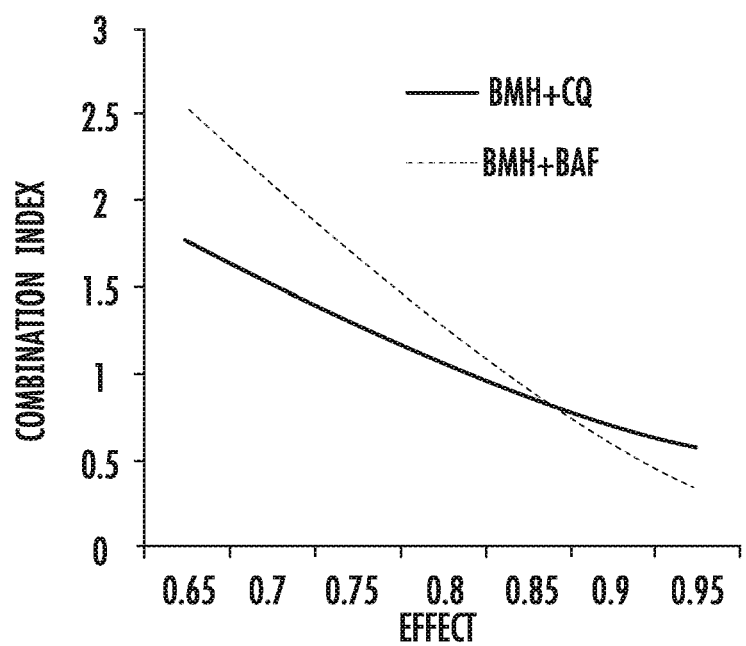
FIGS. 2A-2D show that BMH-21 and autophagy inhibitors chloroquine (CQ) and Bafilomycin (Baf) cause synergistic cell death. (A) MR49F enzalutamide-resistant prostate cancer cells were treated with constant concentrations of BMH-21 and autophagy inhibitors chloroquine or Bafilomycin or their combination for 48 hrs. Cell viability was measured using Cell TiterBlue, and Chou-Talalay Combination Index analysis was performed. CI<1 denotes synergism. Effect denotes the combinatory drug activity where 1 represents 100% kill. (B) MR49F cells were treated with BMH-21 (1 μM), chloroquine or their combination for 24 hrs followed by western blotting for LC3-II. (C) MR49F cells were treated with BMH-21 (1 μM), chloroquine or their combination for 24 hrs followed by staining for LC3-II. (D) Quantification of the number of LC3-II puncta which show a significant increase in the number of puncta following BMH-21 and chloroquine co-treatment.
Figure 2B:
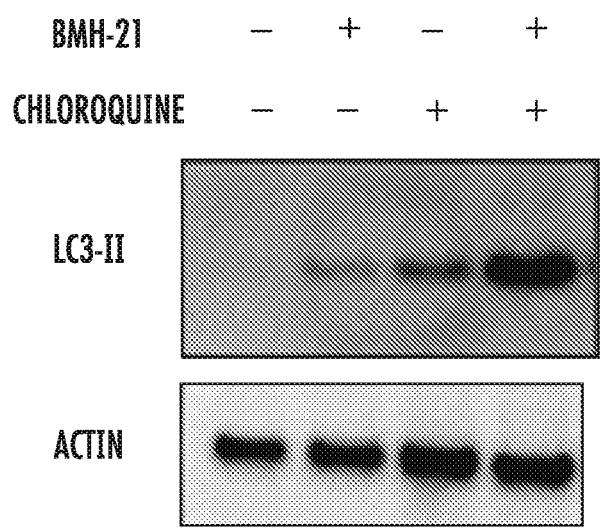
Figure 2C:
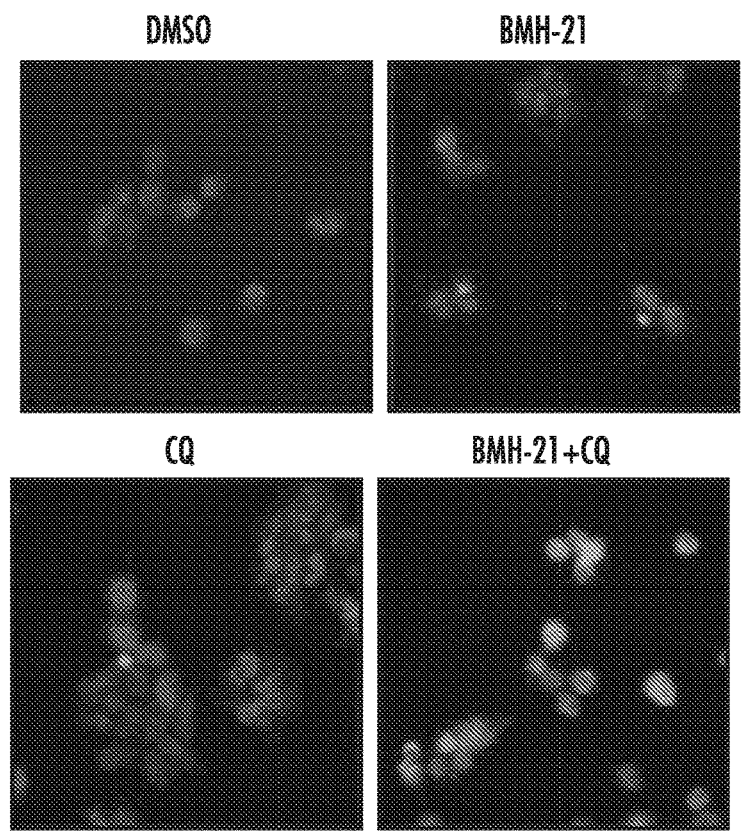
Figure 2D:
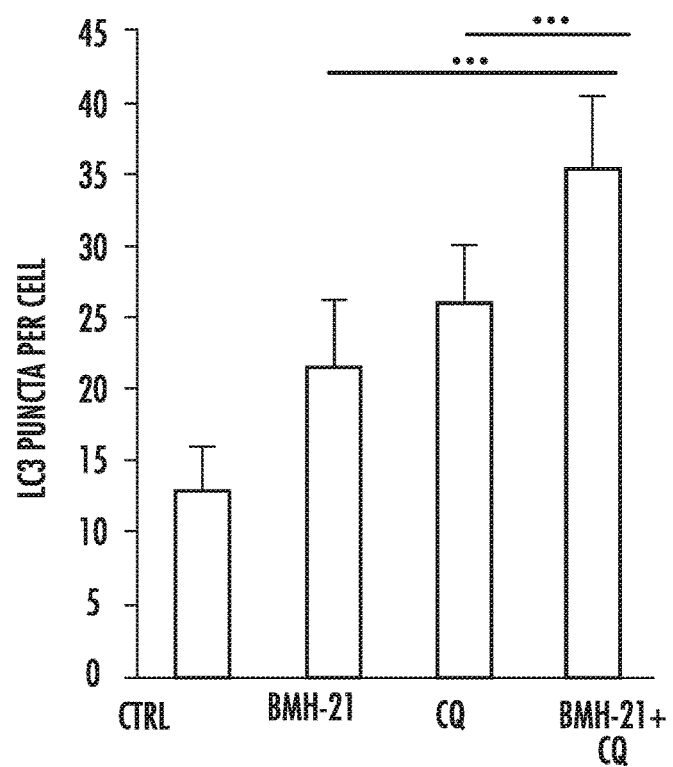

The inventors further tested the combinatory activities of BMH-21 and chloroquine (CQ), an autophagy inhibitor, and more commonly known as an antimalarial, with extensive and well-known medical history. We assessed their combinatory activities on the viability of MR49F enzalutamide-resistant prostate cancer cells and applied Chou-Talalay analysis for the drug interactions. CQ alone was without effect on the viability of the prostate cancer cells. The BMH-21/CQ combination was synergistic in the MR49F cells (FIG. 2A). As shown in FIGS. 2B-2D, the combinatory treatment of BMH-21 and CQ increased the expression of LC3-II, a marker for autophagy inhibition. LC3 was increased by the combination treatment in the MR49F cells as detected by both western blotting and immunofluorescence analysis, and present in the cytoplasm in a typical punctate pattern (FIGS. 2C, 2D). This finding indicates that MR49F cells are dependent on the autophagy pathway. Autophagy-sensitivity of the enzalutamide-resistant cells has recently been proposed by the Evans group (Nguyen et al., 2014), but the combinatory strategy introduced here is novel. We hypothesize that Pol I inhibition leads to a decrease in protein translation due loss of ribosome biosynthesis, unfolded protein response and ER stress, which activate the autophagy pathway and which is needed for cell survival. Two previous reports have observed increased levels of autophagy markers in cells treated with CX-5461 and actinomycin D (Drygin et al, 2011; Katagiri et al., 2015) however, neither report tests nor connects Pol I inhibition to the potential benefit of a combinatory treatment strategy with autophagy inhibition.

Example 3

The Combinatory Effect of BMH-21 and Inhibitors of ACAT1.

Several studies have suggested that altered lipid metabolism is a signature of cancer cells. Given that cholesterol is the main building block for membrane lipids and also a source of steroidogenic hormones, this consideration is especially relevant in cancers of the prostate, breast, liver and pancreas, but also to any other cancer. Lipid droplets are lipid storage organelles that originate from the ER. Free cholesterol, which is toxic to cells, is converted to cholesteryl esters by acyl coenzyme A:cholesterol acyltransferase (ACAT1, encoded by SOAT1), and stored in the lipid droplets (Ikonen et al., 2008; Chang et al., 2009).

Recent data has indicated that high-grade and metastatic prostate cancers have increased levels of esterified cholesterol (Yue et al., 2014). Levels of ACAT1 are increased in prostate cancers and predict biochemical recurrence. It has been speculated that increased ACAT1 expression could promote cholesterol biosynthesis and hence support intratumoral androgen synthesis. Lipids are also a source of cellular energy. Lipid droplets supply fatty acids, which are taken up by the mitochondria for ß-oxidation and ATP production. Cellular lipid droplets can also be degraded by a lipid-specific autophagy process (lipophagy) (Liu and Czaja 2013). Given that autophagy represents a cell survival mechanism by supplementing cell energy sources, we hypothesized that Pol I inhibition could sensitize the cells to block cell survival pathways mediated by lipophagy.

Figure 3A:
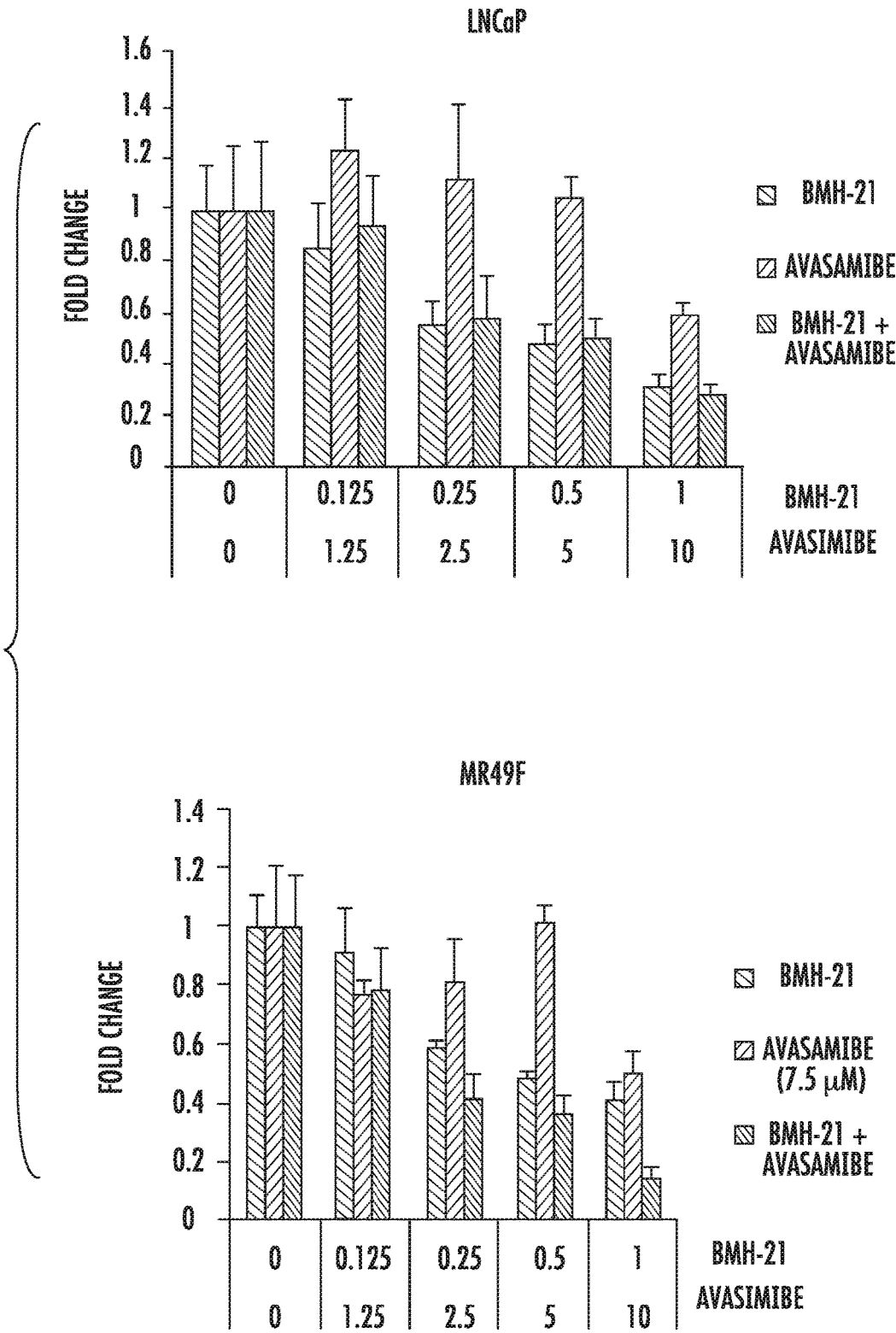
FIGS. 3A-3B illustrate that BMH-21 and Avasimibe cause synergistic cancer cell death. (A) LNCaP and MR49F cells were treated with constant concentrations of BMH-21 and Avasimibe or their combination (μM) for 48 hrs. Cell viability was measured using Cell TiterBlue, and the mean of triplicate samples is shown. (B) Chou-Talalay combination index (CI) analysis was used to determine the drug interactions (blue curve). CI<1 denotes synergism. Red bar, C=1 additive effect. Fraction dead cells denotes the combinatory drug activity where 1 represents 100% kill.
Figure 3B:
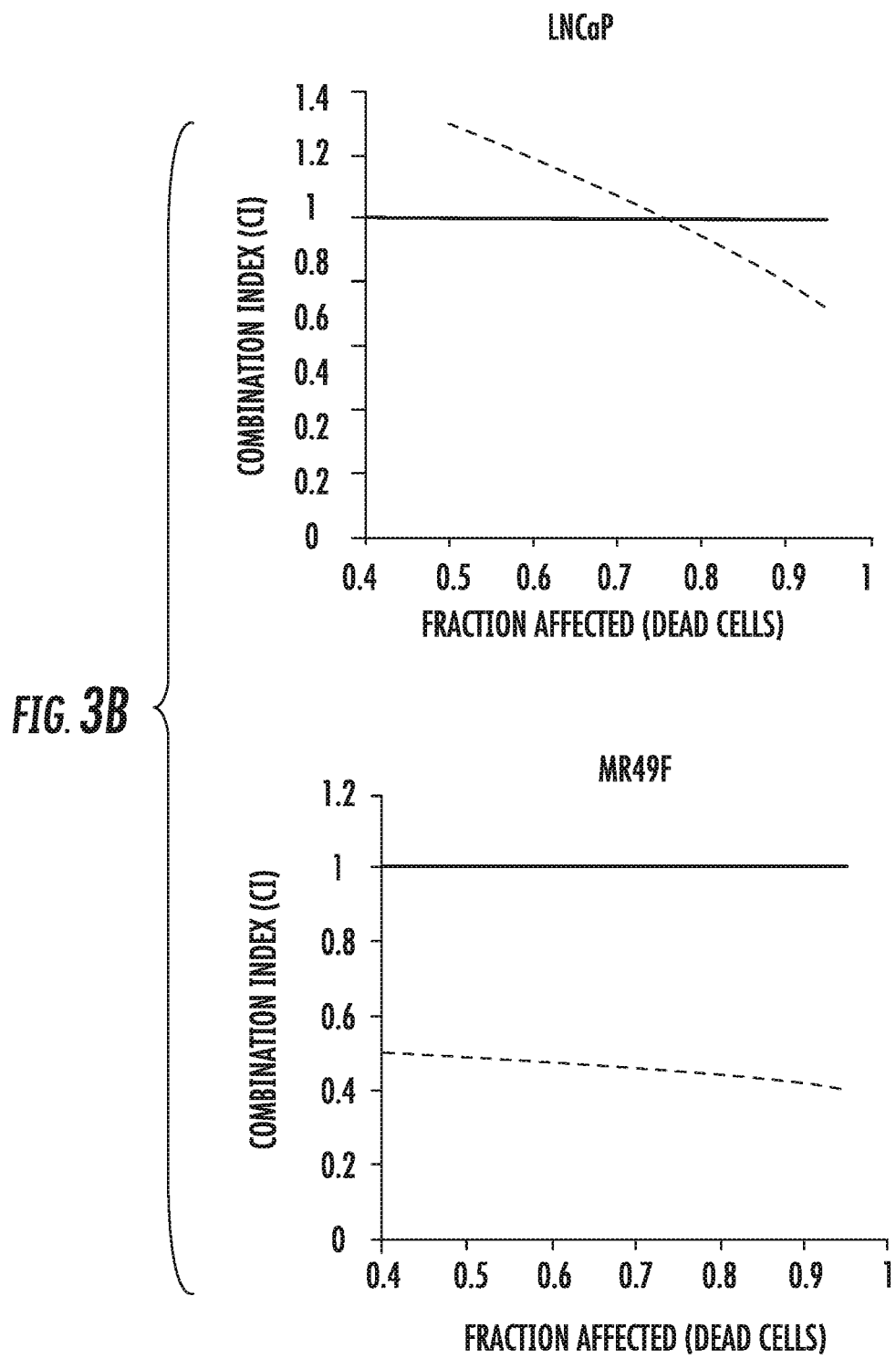
Figure 4A:
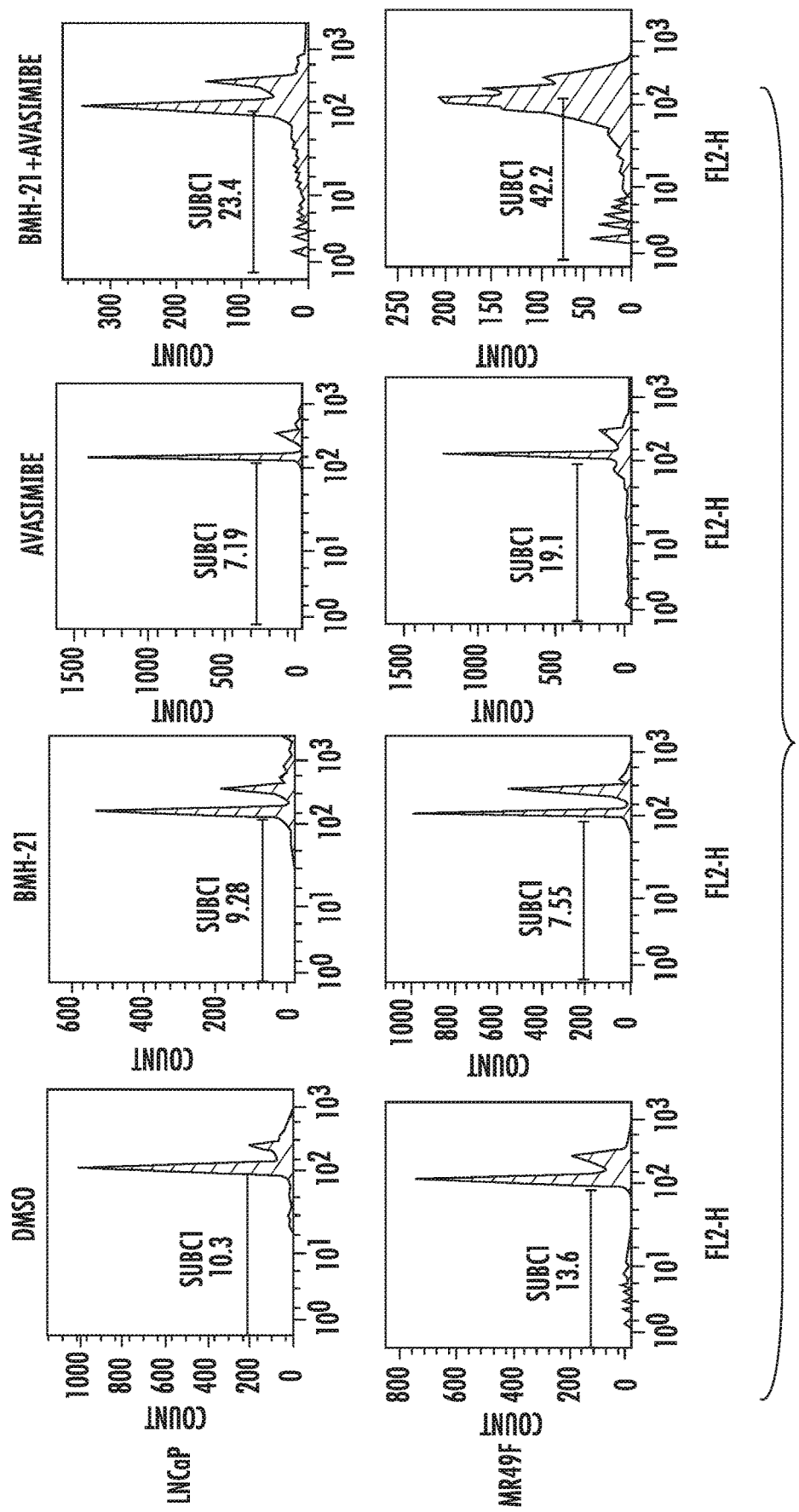
FIGS. 4A-4C illustrate that BMH-21 and Avasimbe cause synergistic prostate cancer cell death. (A) LNCaP and MR49F prostate cancer cells were treated with BMH-21 (1 μM), Avasimibe (7.5 μM) or their combination for 48 hrs followed by flow cytometry. The inset bars represent sub-G1 cells. (B) The percentage of sub-G1 cells from A is plotted over time. (C) Staining of the cells for the apoptosis marker caspase-3.
Figure 4B:
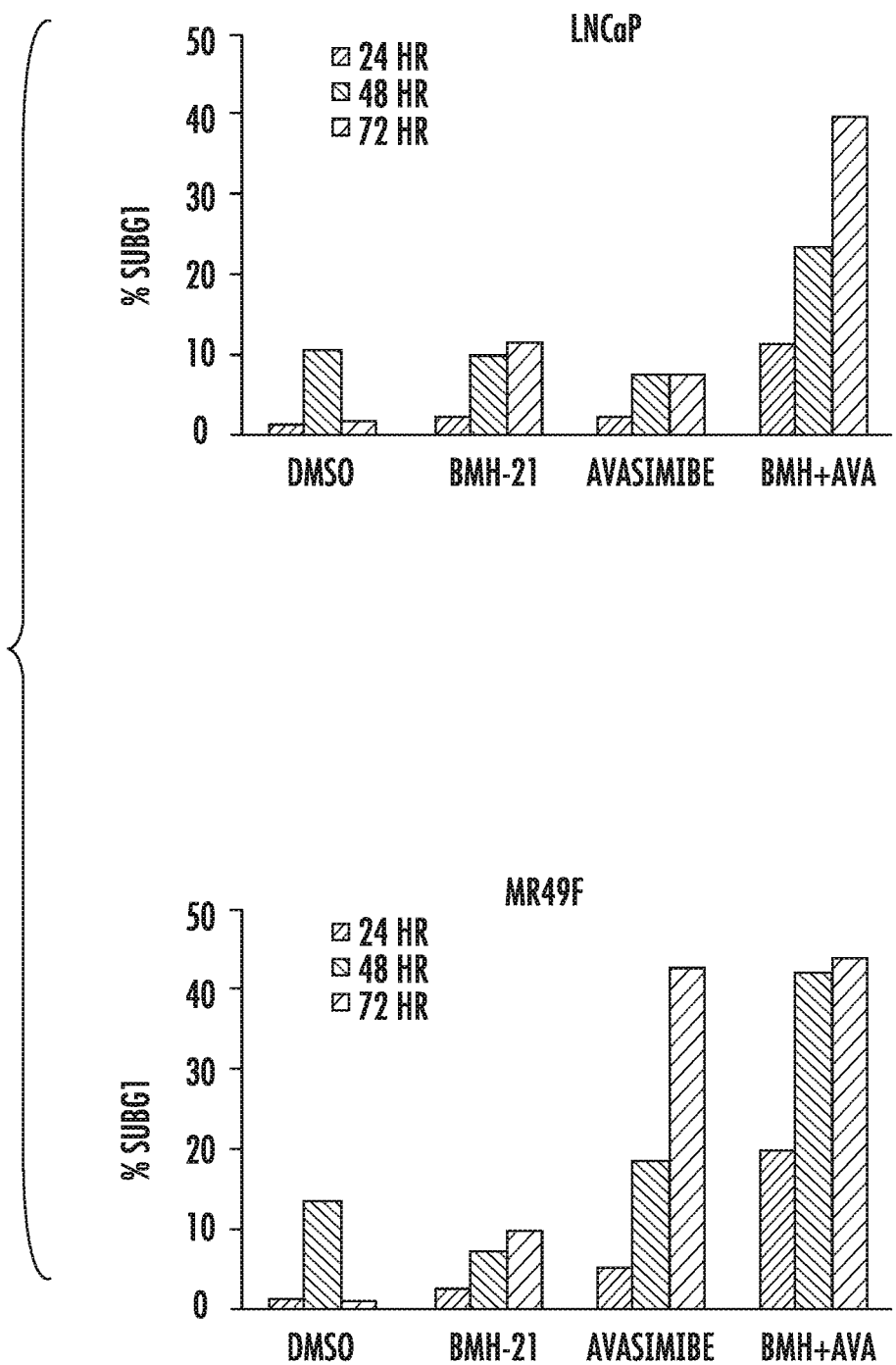
Figure 4C:
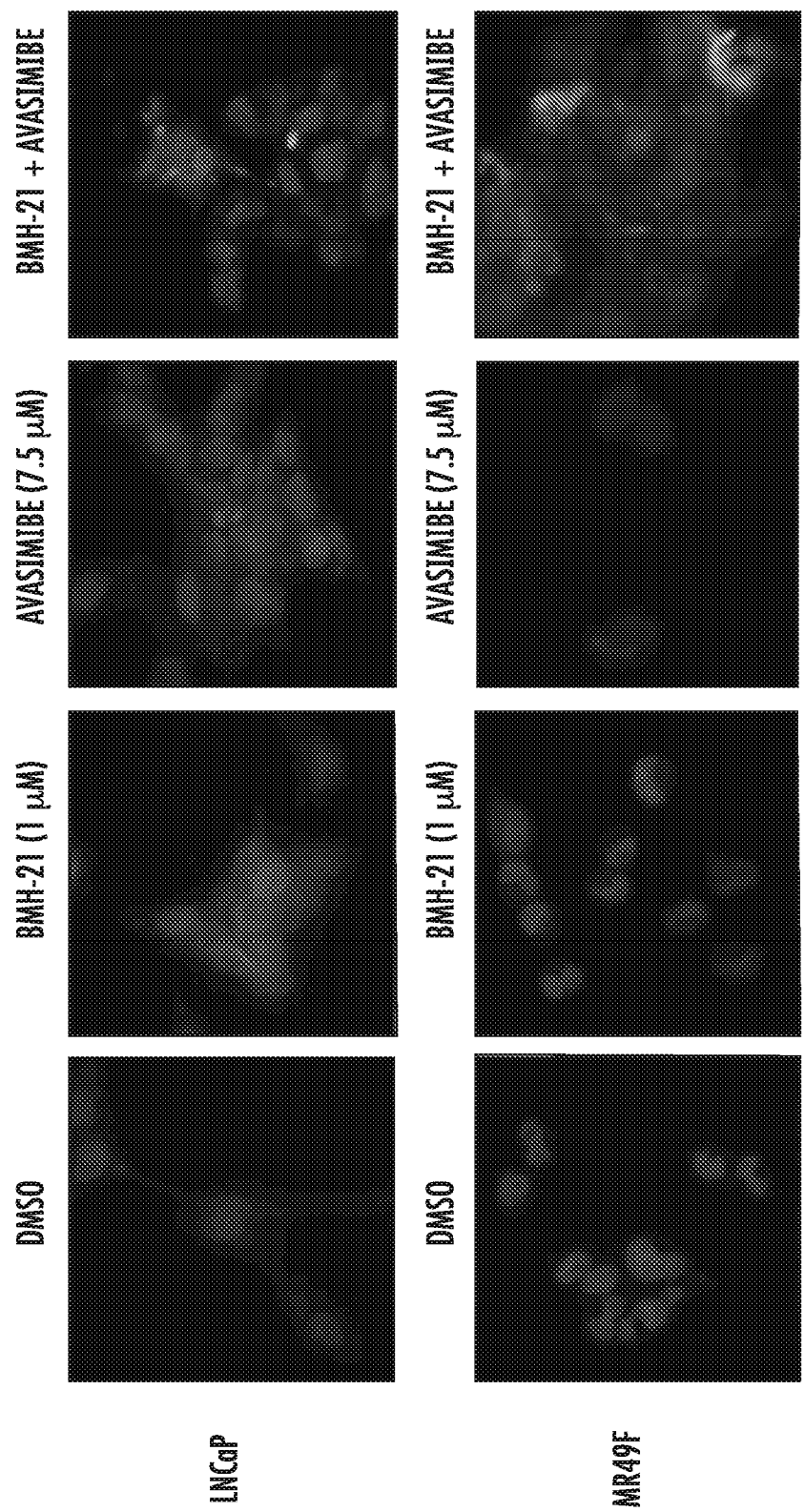
Figure 5A:
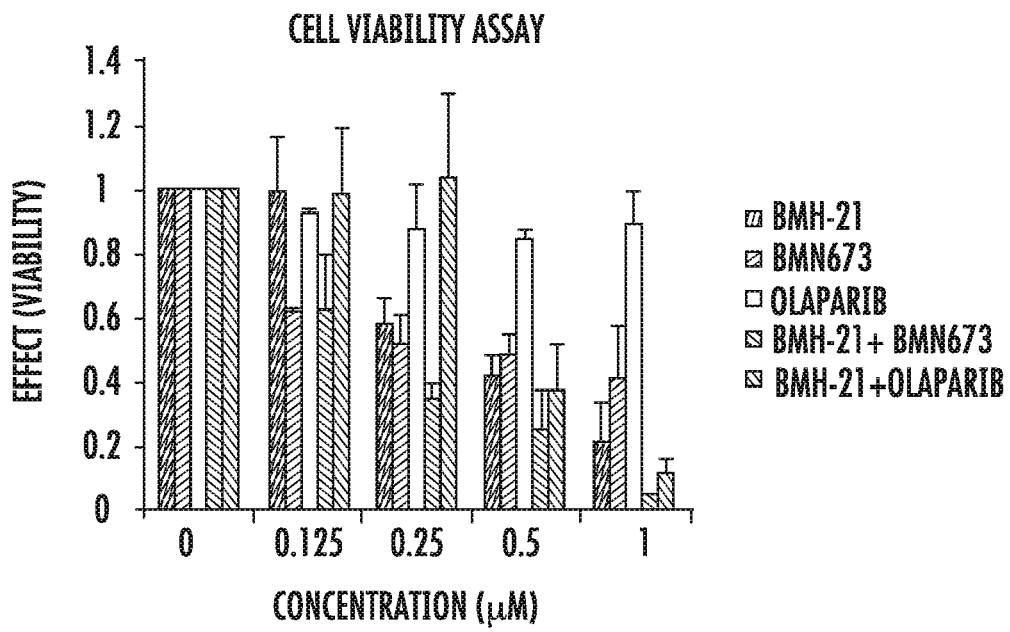
FIGS. 5A-5D show Pol I inhibition by BMH-21 causes strong synergistic cell kill with PARP inhibitors. (A,B) A375 melanoma cells were cultured for 48 h with increasing, constant doses of BMH-21, Olaparib and BMN-673, followed by (A) cell viability assay using CellTiterBlue and (B) analysis of the viability data using Chou-Talalay algorithm. Data represent N=2 biological assays each conducted in triplicate. (C,D) HCT116 p53+/+ and −/− cells were cultured for 48 h with increasing, constant doses of BMH-21, Olaparib and BMN-673, followed by cell viability assay using CellTiterBlue and analysis of the viability data using Chou-Talalay algorithm. Chou-Talalay plots are shown. Data represents N=2 biological assays each conducted in triplicate.
Figure 5B:
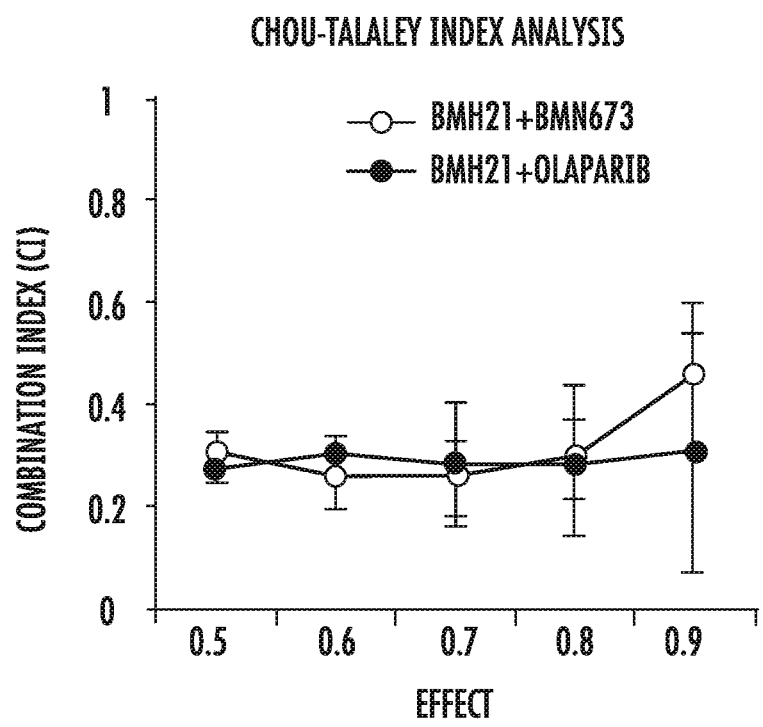
Figure 5C:
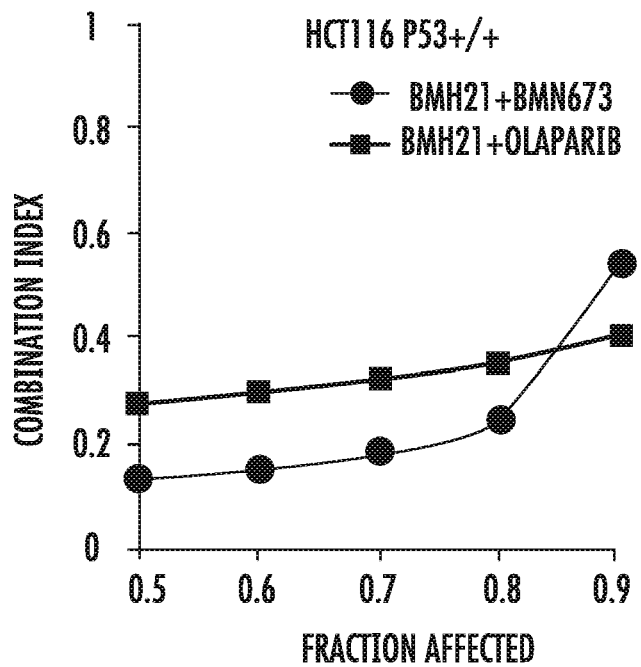
Figure 5D:
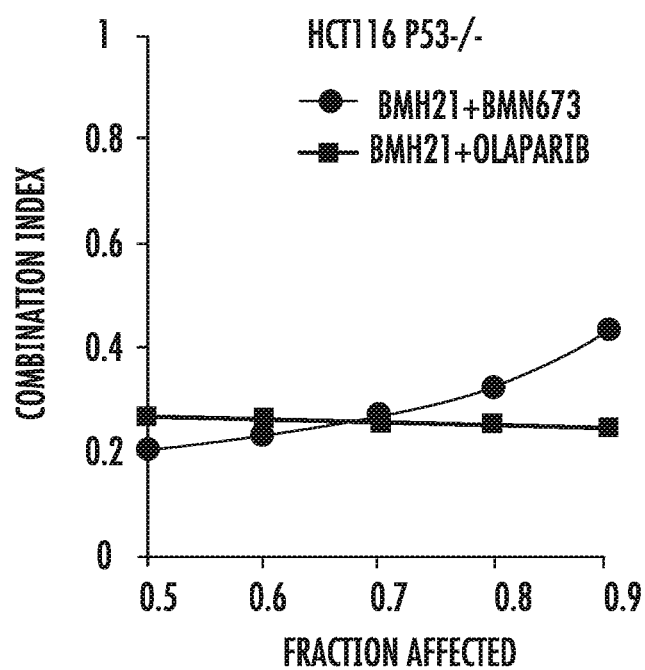

The inventors tested the combinatory activities of BMH-21 and a specific inhibitor of ACAT1, Avasimibe (Lee et al., 1996; Lee et al., 2015). Cell viability assays showed prominent synergistic activities of BMH-21 and Avasimibe in the MR49F cells (FIGS. 3A and 3B). By documenting changes in cell cycle profiles (FIG. 4A) we observed that the combinatory treatments of BMH-21 and Avasimibe caused substantial increase in the sub-G1 fraction of cells by a change of 14% to 42% when compared to the control at 48 hours (FIG. 4B). The increase in the sub-G1 fraction (representing cell death) was especially prominent in the MR49F cells, and was also observed in another MDV3100-resistant LNCaP cell line (data not shown). Visualizing LNCaP and MR49F cells by cleaved caspase-3 staining, and by staining for DNA, revealed prominent cell apoptosis (FIG. 4C). These findings were very striking as the massive apoptotic response was not observed by either treatment alone.

The unexpected component of these findings derive from the observation that there is no previous link between inhibitions of Pol I transcription by small molecule inhibitors and lipid pathway regulators.

Example 4

The Combinatory Effect of BMH-21 and Inhibitors of PARP.

Poly (ADP) ribose polymerase (PARP) is an enzyme that causes reversible modification (PARylation) of proteins, often most rapidly after cellular stresses, most notably following genotoxic stress (Lord and Ashworth 2013). Clinical inhibitors of PARPs are presumed to act by compromising DNA damage repair and by regulation of transcription (Feng et al., 2015). PARP inhibitors have especially been found to be effective in tumors with genetic defects of genes needed for DNA damage repair by homologous recombination, such as BRCA1 and BRCA2. A body of literature documents the role of PARP as a transcriptional repressor (Feng et al., 2015). PARP1 and PARP2 localize to both the nucleus (consistent with their roles as responders to DNA damage and transcription regulators), however, both have also been observed in the nucleolus. PARP1 has been described to bind to silent ribosomal DNA genes, and to increase rDNA silencing (Guetg et al., 2012). Depletion of PARP1 has also been described to increase Pol I transcription (Guetg et al., 2012). However, there are no previous proposals or evidence suggesting a cancer therapeutic strategy by targeting both PARP and Pol I transcription.

The inventors tested these combinations in three different cell lines (A375 melanoma cells, HCT116 p53+/+ and HCT116 p53−/− colon carcinoma cells). In each case we analyzed the cell viability responses to combination treatments with BMH-21 and two PARP inhibitors (olaparib, BMN-673). As assessed by Chou-Talalay combination index analyses, both acted synergistically with BMH-21 in all tested cell lines (FIG. 5). This finding is particularly significant, because it suggests new treatment options in three scenarios: 1) in tumors which have no known defects in DNA repair and are hence not predicted to benefit from PARP inhibitory therapies; 2) in BRCA1/2 mutant tumors with primary; or 3) acquired resistance to PARP inhibitors. Together, the present inventive compositions and methods unravel new combinatory approaches based on our Pol I inhibitory compounds, BMH-21, analogs thereof, and suggest that the combinatory interventions could provide an exceptional therapeutic benefit.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

Laiho M, Peltonen K. U.S. Pat. No. 8,680,107 "Activators and therapeutic applications thereof Laiho M, Barrow J A, Colis L, Ernst G, Sanders S. PCT/US2015/021699 "Compounds which inhibit RNA polymerase, compositions including such compounds, and their use".

Bywater M J, Pearson R B, McArthur G A, Hannan R D. Dysregulation of the basal RNA polymerase transcription apparatus in cancer. Nat. Rev. Cancer 2013; 13:299-314.

Chang T Y, Li B L, Chang C C, Urano Y. Acyl-coenzyme A:cholesterol acyltransferases. Am J Physiol Endocrinol Metab. 2009; 297(1):E1-9.

Chou T C. Drug combination studies and their synergy quantification using the Chou-Talalay method. Cancer Res. 2010; 70:440-6.

Colis L, Ernst G, Sanders S, Liu H, Sirajuddin P, Peltonen K, DePasquale M, Barrow J C, Laiho M. Design, synthesis and structure-activity relationships of pyridoquinazoline-carboxamides as RNA polymerase I inhibitors. J. Med. Chemistry 2014; 57:4950-61.

Drygin D, Lin A, Bliesath J, Ho C B, O'Brien S E, Proffitt C, Omori M, Haddach M, Schwaebe M K, Siddiqui-Jain A, et al. Targeting RNA polymerase I with an oral small molecule CX-5461 inhibits ribosomal RNA synthesis and solid tumor growth. Cancer Res. 2011; 71:1418-30.

Drygin D, Rice W G, Grummt I. The RNA polymerase I transcription machinery: an emerging target for the treatment of cancer. Annu. Rev. Pharmacol. Toxicol. 2010; 50:131-56.

Feng F Y, de Bono J S, Rubin M A, Knudsen K E. Chromatin to Clinic: The Molecular Rationale for PARP1 Inhibitor Function. Mol Cell 2015; 58(6):925-34.

Guetg C, Scheifele F, Rosenthal F, Hottiger M O, Santoro R. Inheritance of silent rDNA chromatin is mediated by PARP1 via noncoding RNA. Mol Cell 2012; 45(6):790-800.

Ikonen E. Cellular cholesterol trafficking and compartmentalization. Nat Rev Mol Cell Biol 2008, 9(2):125-38.

Katagiri N, Kuroda T, Kishimoto H, Hayashi Y, Kumazawa T, Kimura K. The nucleolar protein nucleophosmin is essential for autophagy induced by inhibiting Pol I transcription. Sci Rep. 2015; 5:8903.

Kimura T, Takabatake Y, Takahashi A, Isaka Y. Chloroquine in cancer therapy: a double-edged sword of autophagy. Cancer Res. 2013; 73:3-7.

Lee H T, Sliskovic D R, Picard J A, Roth B D, Wierenga W, Hicks J L, Bousley R F, Hamelehle K L, Homan R, Speyer C, Stanfield R L, Krause B R. Inhibitors of acyl-CoA: cholesterol O-acyl transferase (ACAT) as hypocholesterolemic agents. CI-1011: an acyl sulfamate with unique cholesterol-lowering activity in animals fed noncholesterol-supplemented diets. J Med Chem. 1996; 39(26): 5031-4.

Lee S S, Li J, Tai J N, Ratliff T L, Park K, Cheng J X. Avasimibe encapsulated in human serum albumin blocks cholesterol esterification for selective cancer treatment. ACS Nano. 2015; 9(3):2420-32.

Liu K, Czaja M J. Regulation of lipid stores and metabolism by lipophagy. Cell Death Differ 2013, 20(1):3-11.

Lord C J, Ashworth A. Mechanisms of resistance to therapies targeting BRCA-mutant cancers. Nat Med. 2013; 19(11):1381-8. Nguyen H G, Yang J C, Kung H J, Shi X B, Tilki D, Lara P N Jr, DeVere White R W, Gao A C, Evans C P. Targeting autophagy overcomes Enzalutamide resistance in castration-resistant prostate cancer cells and improves therapeutic response in a xenograft model. Oncogene. 2014; 33(36):4521-30.

Peltonen K, Colis L, Liu H, Trivedi R, Moubarek M S, Moore H M, Bai B, Rudek M A, Bieberich C J, Laiho, M. A targeting modality for destruction of RNA polymerase I that possesses anticancer activity. Cancer Cell 2014; 25:77-90.

Yue S, Li J, Lee S Y, Lee H J, Shao T, Song B, Cheng L, Masterson T A, Liu X, Ratliff T L, Cheng J X. Cholesteryl ester accumulation induced by PTEN loss and PI3K/AKT activation underlies human prostate cancer aggressiveness. Cell Metab.

The invention claimed is:

1. A method of for treatment of a neoplastic disease selected from the group consisting of prostate cancer, colon cancer and melanoma in a subject suffering therefrom comprising administering to the subject an effective amount of a composition comprising a combination of (i) a wherein the compound is selected from the group consisting of:

compound 1

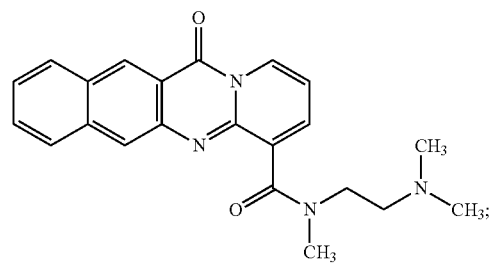

compound 2

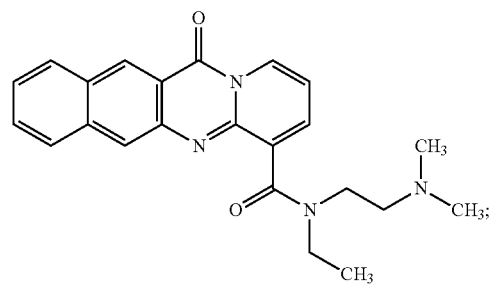

compound 9

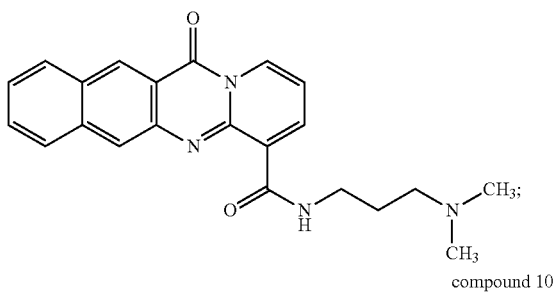

compound 10

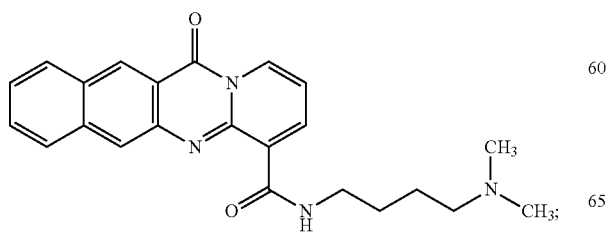

compound 12

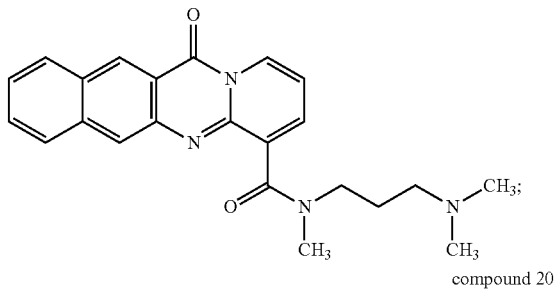

compound 20

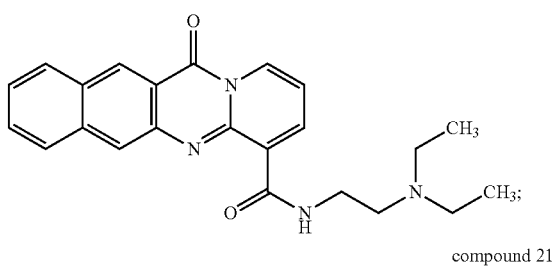

compound 21

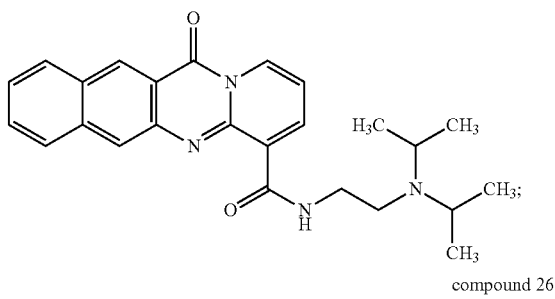

compound 26

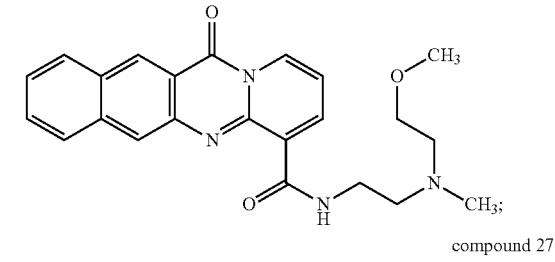

compound 27

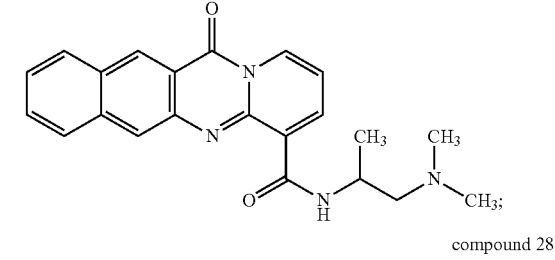

compound 28

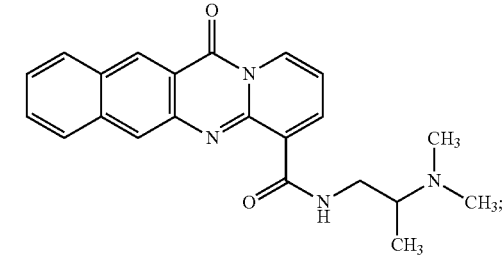

compound 30
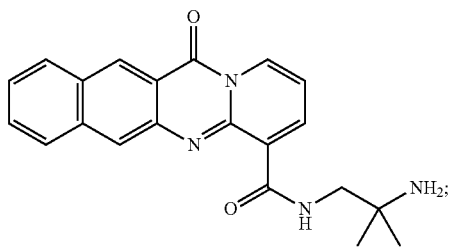

compound 31
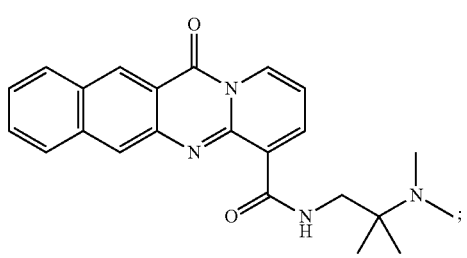

compound 32
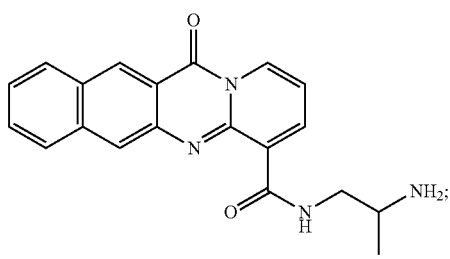

compound 33
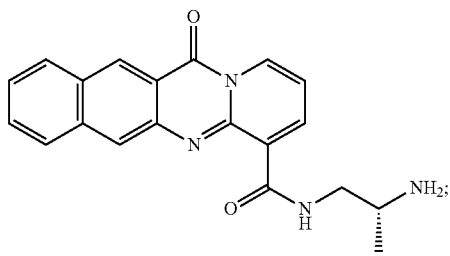

compound 34
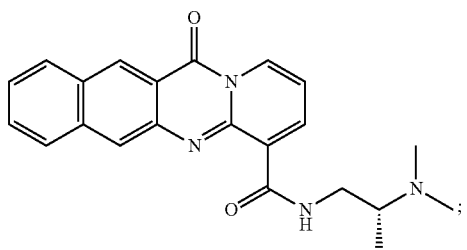

compound 35
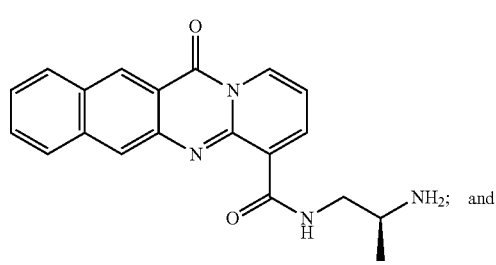

and compound 36
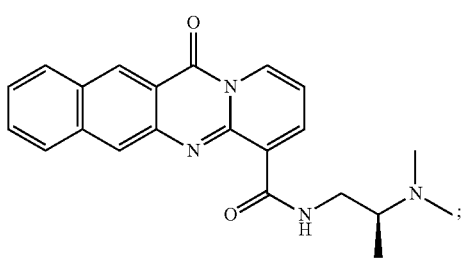

or a pharmaceutically acceptable salt thereof, and (ii) an effective amount of Avasimibe.

2. The method of claim 1, further comprising administering an effective amount of at least one additional therapeutic or chemotherapeutic agent.

3. The method of claim 1, wherein the neoplastic disease is prostate cancer.

4. A method for treatment of a neoplastic disease selected from the group consisting of prostate cancer, colon cancer and melanoma in a subject suffering therefrom comprising administering to the subject an effective amount of a composition comprising a combination of (i) compound is selected from the group consisting of:

compound 1
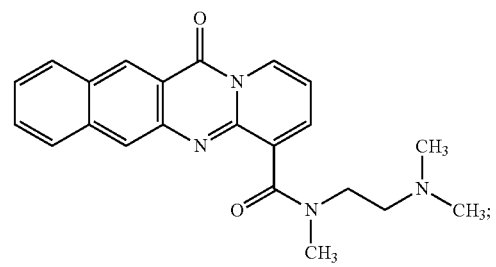

compound 2
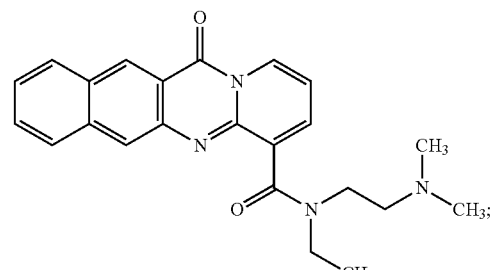

compound 9
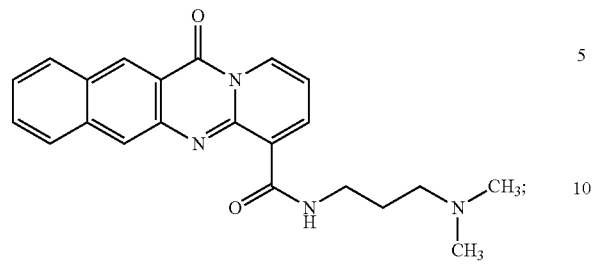
compound 10
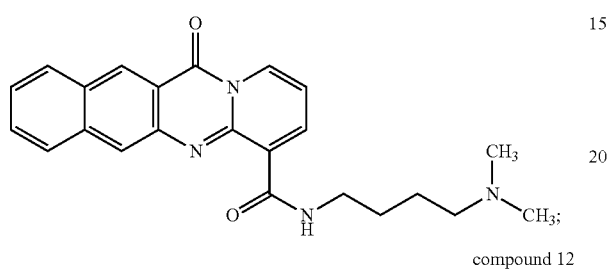
compound 12
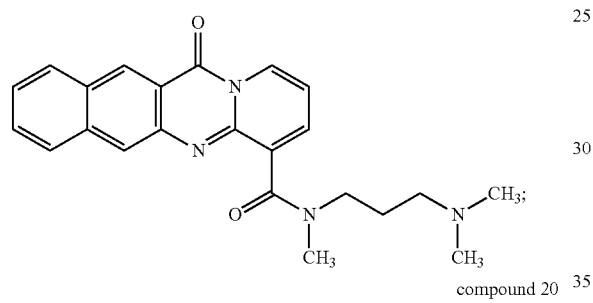
compound 20
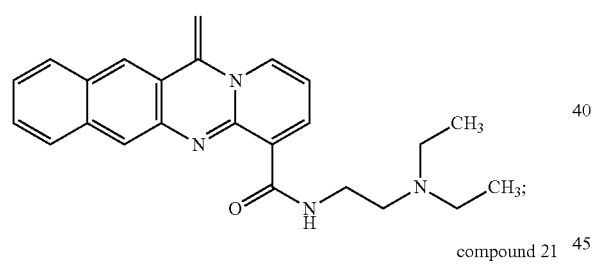
compound 21
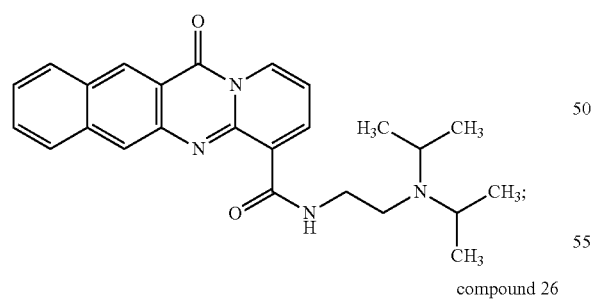
compound 26
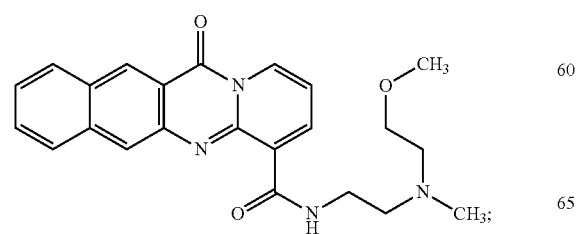
compound 27
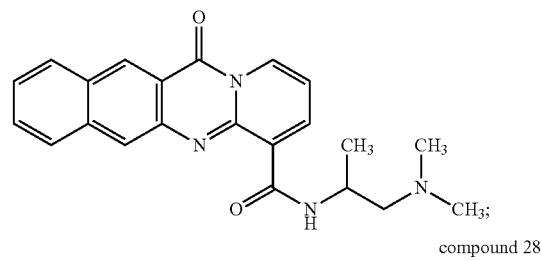
compound 28
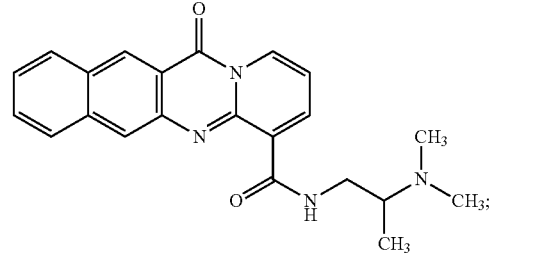
compound 30
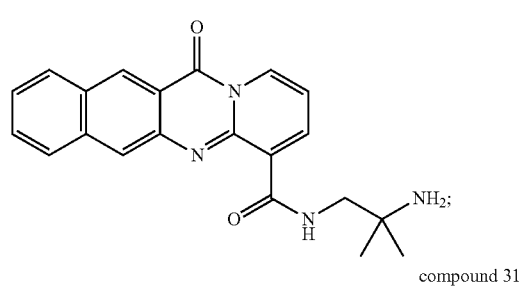
compound 31
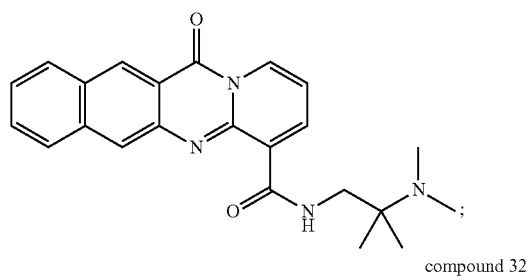
compound 32
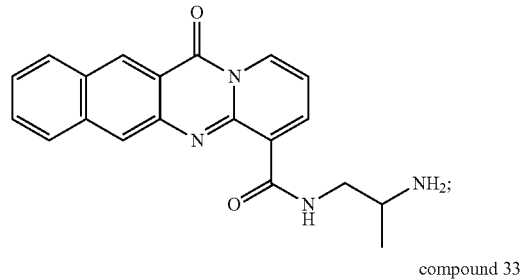
compound 33
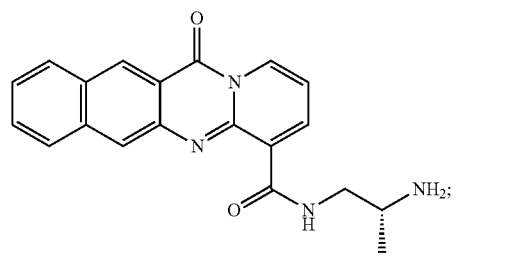

compound 34

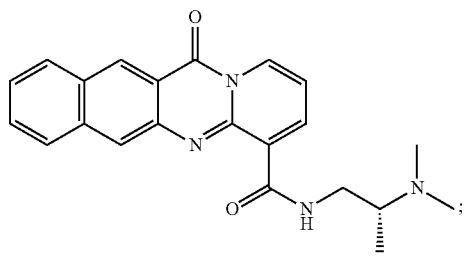

compound 35

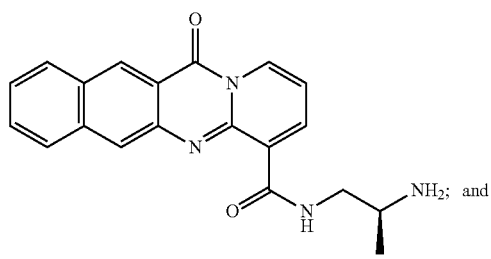

compound 36

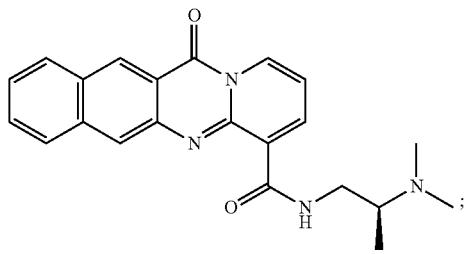

or a pharmaceutically acceptable salt thereof, and (ii) an effective amount of a compound selected from the group consisting of: chloroquine and Bafilomycin A1.

5. The method of claim 4, wherein the neoplastic disease is prostate cancer.

6. A method for treatment of a neoplastic disease selected from the group consisting of prostate cancer, colon cancer and melanoma in a subject suffering therefrom comprising administering to the subject an effective amount of a composition comprising a combination of (i) a compound selected from the group consisting of:

compound 1

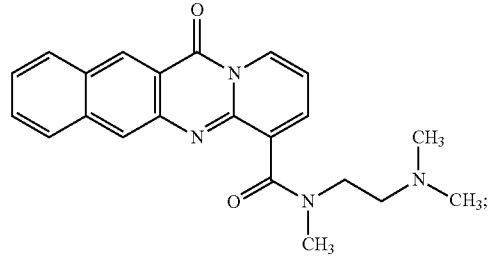

compound 2

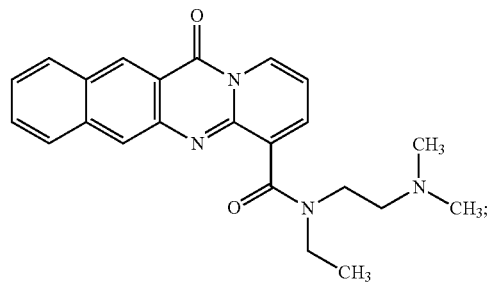

compound 9

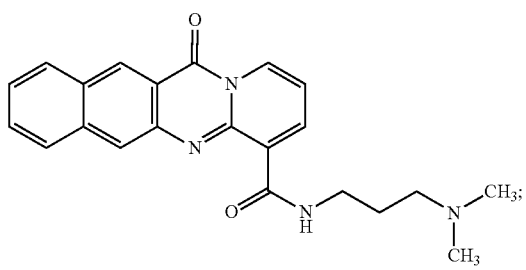

compound 10

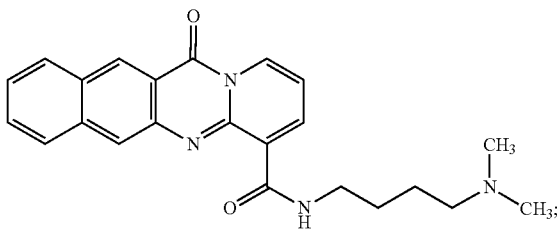

compound 12

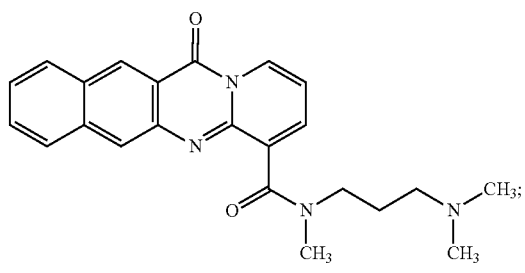

compound 20

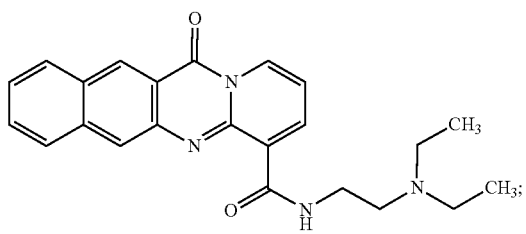

-continued compound 21 compound 26 compound 27 compound 28 compound 30 compound 31

-continued compound 32 compound 33 compound 34 compound 35 compound 36 or a pharmaceutically acceptable salt thereof, and (ii) an effective amount of compound selected from the group consisting of: olaparib and talazoparib.

7. The method of claim 6, wherein the neoplastic disease is melanoma.

8. The method of claim 6, wherein the neoplastic disease is colon cancer.

* * * * *